United States Patent [19]

Keene

[11] Patent Number: 5,541,291
[45] Date of Patent: Jul. 30, 1996

[54] METHODS AND COMPOSITIONS USEFUL IN THE DIAGNOSIS AND TREATMENT OF AUTOIMMUNE DISEASES

[75] Inventor: Jack D. Keene, Durham, N.C.

[73] Assignee: Duke University, Durham, N.C.

[21] Appl. No.: 54,871

[22] Filed: May 27, 1987

Related U.S. Application Data

[63] Continuation-in-part of Ser. No. 687,908, Dec. 31, 1984, abandoned.

[51] Int. Cl.⁶ .................. C07K 14/47; C12N 15/00; A61K 38/16
[52] U.S. Cl. .................. 530/350; 435/172.3; 530/358
[58] Field of Search .................. 530/300, 324, 530/325, 350, 353, 358, 806

[56] References Cited

U.S. PATENT DOCUMENTS 4,865,970  9/1989  Brot .................. 435/7

FOREIGN PATENT DOCUMENTS

| 0140308 | 5/1985 | European Pat. Off. . |
|---|---|---|
| 0223399 | 5/1987 | European Pat. Off. . |
| 8301451 | 4/1983 | WIPO . |
| 8703451 | 6/1987 | WIPO . |

OTHER PUBLICATIONS

Proc. Natl. Acad. Sci, vol. 75, No. 1, Jan. 1978, pp. 280–284 US, P.C. Zamecnik et al: "Inhibition of Rous Sarcome Virus Replication and . . . ".
Proc. Natl. Acad. Sci, vol. 75, No. 1, Jan. 1978, pp. 285–288, US, M. L. Stephenson et al: "Inhibition of Rous Sarcoma Viral RNA Translation by a . . . ".
J. Theor. Biol., vol. 113, No. 2, Mar. 21, 1985, pp. 395–405, Acad. Press, Inc., London, GB, J. C. Sanford et al: "The Concept of Parasite Derived . . . ".
Tan. Advances in Immunology, vol. 33, pp. 167–221 1982.
Venables et al. Clin Exp. Immunol 54: 731, 1983.
Chambers et al PNAS 82:2115, 1985.
Miller et al EMBO J 4:1609–1614 1985. Repetitive Zinc binding domains in the protein transcription of factor III A from *Xenopus oocytes*.
Hans H. Guldner, et al, The Journal of Immunology, vol. 141, No. 2, Jul. 15, 1988, Epitope Mapping With A Recombinant Human 68-KDa (U1) . . . .
Allan D. Sturgess, et al, Journal of Immunology, vol. 140.3212, Characteristics and Epitope Mapping of a Cloned Human Autoantigen La . . . .
Peter D'Arpa, et al, Proc. Natl. Acad. Sci. USA, vol. 85, pp. 2543–2547, Apr. 1988, Biochemistry, cDNA Cloning of Human DNA Topoisomerase I: . . . .
Luis A. Rokeach, et al, Proc. Natl. Acad. Sci. USA, vol. 85, pp. 4832–4836, Jul. 1988, Immunology, Molecular Cloning of a cDNA Encoding the Human . . . .
Wm. C. Earnshaw, et al, Proc. Natl. Acad. Sci, Use, vol. 84, pp. 4979–4983, Jul. 1987, Immunology, Analysis of Anti-centromere Autoantibodies Using . . . .
Hans Jurgen Netter, et al, Arthritis and Rheumatism, vol. 31, No. 5, (May 1988) a Recombinant Autoantigen Derived From the Human (U1) Small Nuclear RNP . . . .
Winand J. Habets, et al, Proc. Natl. Acad. Sci. Use, vol. 84, pp. 2421–2425, Apr. 1987, Immunology, Analysis of a cDNA Clone Expressing a Human . . . .
Senga Whittingham, et al, The Lancet, Saturday, Jul. 4, 1987, Serological Diagnosis of Primary Sjogren's Syndrome by Means of Human Recombinant La . . . .
Benjamin E. Rich, et al, Molecular and Cellular Biology, Nov. 1987, pp. 4065–4074, vol. 7, No. 11, Human Acidic Ribosomal Phosphoproteins P0, P1 and P2 . . . .
Peter T. G. Sillekens, et al, The EMBO Journal, vol. 6, No. 12, pp. 3841–3848, 1987, cDNA Cloning of the Human U1 snRNA–Associated a Protein: Extensive . . . .
Spritz, et al, Nucleic Acids Research, pp. 10373–10390, Human U1-70K snRNP Protein: cDNA Cloning, Chromosomal Localization, Expression . . . .
David R. Stanford, et al, The Journal of Biological Chemistry, vol. 262, No. 21, Issue of Jul. 25, pp. 9931–9934, 1987, DNA Sequence of a Human Sm . . . .
Hubert Theissen, et al, IRL Press Limited, pp. 3209–3217, Cloning of the Human cDNA for the U1 RNA–Associated 70K Protein.
*Science*, vol. 231, pp. 737–740.
*Proc. Natl. Acad. Sci.*, vol. 85, pp. 2543–2547, Apr. 1988 .
*The Journal of Biological Chemistry*, vol. 262, No. 21, Issue of Jul. 25, pp. 9931–9934, 1987.
*Cell*, vol. 53, 675, Jun. 3, 1988.
Cloning of the human cDNA for the U1 RNA–associated 70K protein, Theissen et al.
*Proc. natl. acad. sci.*, USA 85 (1988) Biochemistry: Deutscher et al pp. 9479–9483.
*Cell*, vol. 57, 89–101, Apr. 7, 1989, A Common RNA Recognition Motif Identified within a Defined U1 RNA Binding Domain of the 70K U1 snRNP Protein.

*Primary Examiner*—Suzanne E. Ziska
*Attorney, Agent, or Firm*—Oblon, Spivak, McClelland, Maier & Neustadt, P.C.

[57] ABSTRACT

A method for producing a protein antigen which is reactive with an autoantibody associated with an autoimmune disease in a host, which comprises introducing genetic information from a cross-reactive donor gene library, into plural cells thereby producing transformed cells: selecting a producer cell which expresses said antigen by detecting a binding reaction between said autoantibody obtained from said host and a protein antigen expressed by a producer cell of said transformed cells which contains a gene coding for said protein antigen, thereby identifying a cloned DNA segment from said donor which can be utilized in the production of said protein, is disclosed along with biochemical reagents and products associated with this invention.

1 Claim, 7 Drawing Sheets

METHODS AND COMPOSITIONS USEFUL IN THE DIAGNOSIS AND TREATMENT OF AUTOIMMUNE DISEASES

This application is a continuation-in-part of application Ser. No. 06/687,908 filed Dec. 31, 1984, now abandoned.

The investigations leading to the present invention were supported in part by a grant from the National Institutes of Health.

BACKGROUND OF THE INVENTION

1. Field of the Invention:

The present invention relates to methods and compositions useful in the treatment and diagnosis of autoimmune diseases and more particularly to such methods and compositions produced by genetic engineering.

2. Description of the Prior Art:

In normal humans and animals an individual will respond to exposure to a foreign substance by the production of specific antibodies or by developing cell-mediated immunity against the foreign substance. Individuals are generally tolerant of substances which normally form a part of themselves and are thus described as being self-tolerant. The development of an immunologic response to self is called autoimmunity and is the result of some breakdown of self-tolerance.

Various theories have been proposed to explain the development of autoimmunity. For example, viruses are thought to play an important role in the pathogenesis of autoimmunity as has been demonstrated in several animal models. The expression of viral antigens on the surface of the host cells may elicit autoantibodies to cell antigens as well as to the viral antigens. It has also been proposed that autoimmunity is a disorder caused by abnormal immunologic regulation, particularly a change in T-cell activity. A decrease in suppressor T-cell activity or an increase in helper T-cell activity would result in excess production of autoantibodies. This theory finds support in the finding of autoantibodies in some normal persons without evidence of autoimmune disease and in various animal models. Gene control also appears to exist in at least some autoimmune diseases as certain micestrains have been demonstrated to exhibit an autoimmune disease similar to systemic lupus erythematosus (SLE). A high correlation of SLE is also found in identical twins. Additionally, an association of autoimmune disease with genes located in the HLA-D locus has been noted in adult rheumatoid arthritis and in multiple sclerosis.

Systemic lupus erythematosus (SLE) is a serious autoimmune disease which affects the collagen of the connective tissues of the human body. Since SLE may affect one or more of a large number of different tissues or organs of the body, such as blood vessels, heart, kidneys, skin, serous membranes, etc., clinical diagnosis of SLE is often difficult since the symptoms may resemble a number of other diseases such as rheumatoid arthritis, skin cancer, serum sickness, rheumatic fever, multiple myeloma, and Sjogren's syndrome.

It is important to be able to distinguish SLE from other diseases due to the high probability of kidney, central nervous system, and vascular damage from the disease. For example, lupus nephritis is very frequent in the disease and is one of the most serious features of SLE. Nephritis is a frequent cause of death in SLE patients, and it would be most advantageous to be able to detect SLE early enough to prevent or mitigate serious kidney damage.

It has been demonstrated that sera from patients with connective tissue disorders contain antibodies to many nuclear constituents. For example, circulating antibodies that react with native DNA (deoxyribonucleic acid) have been found to be highly specific to patients suffering from systemic lupus erythematosus. The appearance and exacerbation of the nephritis attendant in SLE appears to be related to the formation and deposition of antibody/DNA and other immune complexes in the kidneys and particularly the renal glomeruli. Although the exact reasons for the production of these antibodies and the reasons for their particular specificity to SLE are as yet unknown, the detection and measurement of these autoantibodies has become increasingly important in the clinical diagnosis and evaluation of this disease.

Recently, a precise method for measuring various small amounts of anti-DNA antibody has been developed using $C^{14}$-labeled DNA. See T. Pincus et al, "Measurement of Serum DNA-Binding Activity In Systemic Lupus Erythematosus," *New England Journal of Medicine*, 281,701–705 (1969). This method appears to be the most definitive test for SLE presently available. It is reported to be positive in 75 percent of SLE patients studied, whereas other leading tests were positive in only about 25–64 percent of SLE cases. Moreover, this anti-DNA antibody test has shown greater specificity for SLE than other diagnostic tests used, such as immunodiffusion, complement-fixation, and precipitation. Normal sera also often reacts with DNA.

However, this test is a test for antibodies that react with DNA although DNA may not be the authentic antigen. Furthermore, this method is not applicable to autoimmune disorders in which the antigen is a protein. Protein antigens are associated with most forms of SLE as well as other types of autoimmune diseases. Such protein antigens are useful in disease classification, diagnostic and treatment methods as a result of the ability to react specifically with autoantibodies associated with an autoimmune disease. However, isolation and purification of these antigens have heretofore not been fruitful because of the scarcity and instability of antigenic material and because of the complexity of the separation techniques. Accordingly, a method for producing protein antigens which are reactive with an autoantibody associated with an autoimmune disease in a host is still needed.

SUMMARY OF THE INVENTION

It is an object of this invention to provide a method for producing a protein antigen which is reactive with an autoantibody associated with an autoimmune disease.

It is a further object of this invention to provide a method for readily providing a protein antigen reactive with an autoantibody associated with an autoimmune disease.

It is a further object of this invention to provide a method capable of producing such antigens in large amounts and without requiring donation of large amounts of material from a host.

It is a further object of this invention to provide a method for readily providing high quantities of such a protein antigen without requiring donation of large amounts of material from a host.

It is a further object of this invention to provide a method for readily providing high quantities of such a protein antigen having a high degree of purity.

These and other objects of the invention as will hereinafter become more readily apparent have been accomplished by providing a method for production of a protein antigen which is reactive with an autoantibody associated with autoimmune disease in a host. This method comprises introducing genetic information from a crossreactive donor gene library into plural recipient cells, thereby giving transformed cells. A cell which expresses the antigen is selected by detecting a binding reaction between said autoantibody obtained from said host and a protein antigen expressed by a producer cell of said transformed cells which contains a gene coding for said protein antigen. This cell which expresses the antigen is cultivated in a culture medium, and the protein antigen is isolated from the culture medium.

It is also an object of this invention to provide recombinant DNA molecules useful in the practice of the method of the invention as well as methods of using the protein antigens, now available for the first time in large quantities, for the diagnosis and treatment of autoimmune diseases.

It is also an object of this invention to provide the protein antigens obtained from the process of this invention.

BRIEF DESCRIPTION OF THE DRAWINGS

A more complete appreciation of the invention and many of the attendant advantages thereof will be readily obtained by reference to the following detailed description when considered in connection with the following figures.

DESCRIPTION OF THE PREFERRED EMBODIMENTS

Figure 1A:
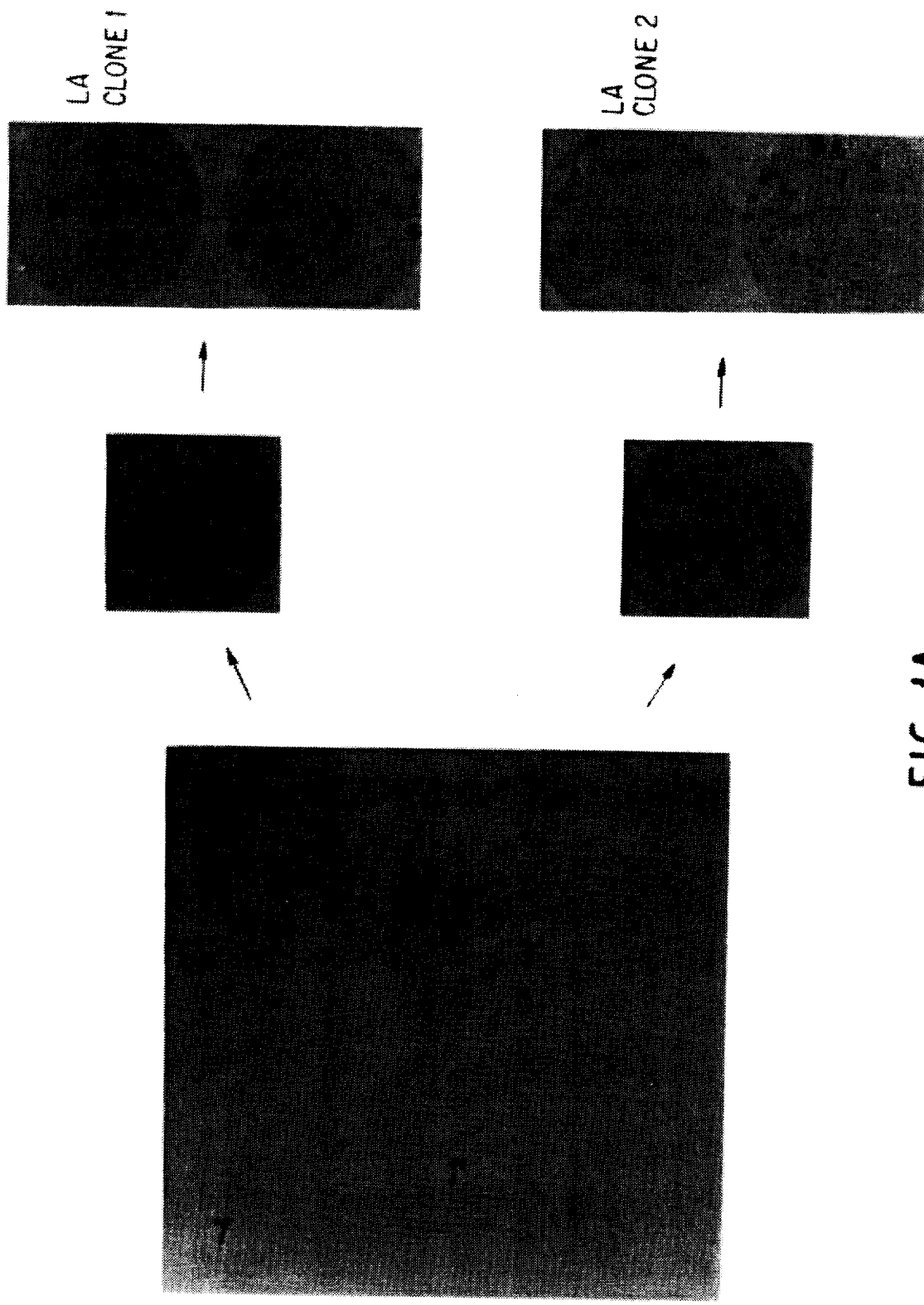
FIG. 1(a) is a series of photographs of culture media showing isolation and identification of La cDNA clones by immunological screening of λgtll recombinant phage plaques with lupus sera of the La specificity.

The present invention arose in part with the recognition that several cDNA clones obtained from a human liver expression library were recognized by autoantibodies associated with certain autoimmune disorders. Prior to the present invention it was not known that peptides reactive with autoimmune antibodies could be produced in this manner. Additionally, if a physician or investigator wanted an antigen from a particular patient or other affected individual, it was necessary to isolate the antigen from that source. Such antigens were generally not free in solution and were in any event available in only minute quantities, making this identification, analysis, and use practically impossible, since the production of large quantities of antigen required large quantities of material from the affected human or animal, to the detriment of that individual.

This procedure succeeded because the autoantibodies did not react with proteins of E.coli, nor did they react with DNA of E.coli during the screening experiments, but only with the expressed human protein.

Since the source which donated the original messenger DNA from which the cDNA clones were produced in the inventor's laboratory was not the same as the source of the autoantibodies, it was recognized that protein antigens which are reactive with autoantibodies associated with an autoimmune disease, which were not previously available in large quantities, could be produced requiring no more than a serum sample from a host having an autoimmune disease by reacting the serum or antibodies derived therefrom with a cDNA library from a different source. Accordingly, the present invention makes available for the first time an effective means for treating autoimmune diseases in a host in a manner specific for that host.

By "host" is meant any human or animal afflicted with an autoimmune disease. Although the invention was first demonstrated with a human host and it is anticipated that human hosts will remain an area of interest, the present invention can also be used in the field of veterinary medicine. For example, horses, cattle, sheep, and fowl (e.g., chickens, ducks, and turkeys), primates, dogs, cats, pigs, goats (especially for treatment of goat arthritis), and mink (especially for treatment of Aleutian mink disease).

One reagent used in the practice of the invention is antiserum (or a purified antibody) from the host serum. A serum or plasma sample is obtained from a host, typically by veinipuncture, and red blood cells and clots are removed. Antibodies are then separated from other proteins by any suitable technique. The antigenic reactivity of the host is determined by immunoprecipitation of radio labelled host-cell extracts or by immunoblotting of unlabelled host-cell extracts. In both cases the reactive antigens are characterized by molecular weight fractionation (acrylamide gel electrophoresis) and bonding of immuno complexes to protein A from *Staphylococcus aureus* as described in Towbin et al, *Proc. Natl. Acad. Sci. USA*, 76, 4350–4354 (1979) and Francoeur et al, *Proc. Natl. Acad. Sci. USA*, 79, 6772–6776 (1982), although many other methods for carrying out these reactions are equally suitable.

Another reagent needed for the practice of the present invention is a gene library from a donor species sufficiently related to the host so as to produce a cross-reactive protein antigen. As used in this specification, "gene library" refers to a collection of vectors having operationally inserted therein or attached thereto DNA fragments from a cell or cells of the donor species. Since the host and donor, as described in this specification, are eucaryotic organisms, complementary DNA (cDNA) libraries are particularly preferred although not necessary since antigenic determinants may be present on proteins produced from DNA segments which contain both introns and functional gene segments when these DNA segments are expressed as peptides in recipient unicellular organisms. However, it is well recognized that cDNA produced from messenger DNA and thereby lacking the introns which are normally present in eucaryotic cells has a higher success rate in expressing proteins when inserted into procaryotic recipient cells, and use of a cDNA library is accordingly preferred.

It will be recognized by those skilled in the art, armed with the disclosure set forth in this specification, that the donor species need not be the same as the host species. However, it is required that the donor species be capable of expressing a protein having an antigenic site (determinant) cross-reactive with the autoantibody of the host. Selection of a donor species can easily be accomplished by radioactively labeling cultured cells from a proposed donor species (with, for example, 35S methonine), preparing a crude cell extract from the cultured cells, and immunoprecipitating the cell extract with autoantibody obtained from the host together with protein A from *Staphylocoeus aureas*. If radioactivity is precipitated, an antigen is present in the donor cell extract that is reactive with the autoantibody obtained from the host, and the gene library from this donor can be used in the method of the invention. Alternatively, the donor species or a specific tissue from the donor can be extracted, and the extracted proteins can be fractionated in a matrix. The separated proteins are immobilized by transfer to a membrane and reacted with the autoantibody from the host. If protein A from *Staphylococcus aureus* binds to the filter, a corresponding gene library from the donor tissue can be used in the method of the invention. Nevertheless, in order to increase the percentage of producer cells (cells which produce a suitable protein antigen) in a given transformation, it is preferred that the donor and the host be in the same genus, preferably in the same species, although use of a mammalian donor with a mammalian host is also suitable.

By "cross-reactive" in this application is meant that an autoantibody of the host reacts with a protein antigen produced by the donor. This donor protein antigen need not be identical with the normal protein antigen present in the host that provides the antigenic determinant for the autoantibody associated with the autoimmune disease of the host. Cross-reacivity is defined by the ability of the antigen in question to react with the autoantibody. Naturally, if the protein antigens are identical, cross-reactivity will exist. In SLE, greater than one half of all patients demonstrate autoantibodies reactive with one of these four major specificities or classes. Methods as described herein will allow those experienced in the art to produce purified antigens of each class as general diagnostic or therapeutic reagents for other individuals containing autoantibodies of the same specificity or class.

The phrase "genetic information" generally refers to DNA which codes for all or part of the protein antigen. However, this phrase also encompasses RNA when used with an RNA virus or other vector based on RNA.

A cell which has received genetic information coding for the protein antigen and which expresses the protein antigen whether retained intracellularly or released into the culture medium, is referred to as a "producer cell."

The term "vector" is well understood and is synonymous with the often-used phrase "cloning vehicle". A vector is non-chromosomal double-stranded DNA comprising an intact replicon such that the vector is replicated when placed within a unicellular organism, for example by a process of transformation.

A material is "purified" when it does not contain other components that would interfere with the reactivity or property being sought and that would be present in the material as naturally formed. More preferably, purified material contains at least 95% by weight, even more preferably 99%, and most preferably 99.8%, of a single material. Water is not counted in measuring purity.

Advances in biochemistry in recent years have led to the construction of "recombinant" vectors in which, for example, plasmids are made to contain exogenous DNA. In particular instances the recombinant vector can include heterologous DNA, by which is meant DNA that codes for a polypeptide ordinarily not produced by the organism susceptible to transformation by the recombinant vector. The production of recombinant DNA vectors in the process of producing a gene library is well understood and need not be described in detail. However, a brief description of this process is included here for reference.

For example, a plasmid vector can be cleaved to provide linear DNA having ligatable termini. These termini are bound to exogenous DNA having complementary like ligatable termini to provide a biologically functional recombinant DNA molecule having an intact replicon and a desired phenotypical property. A variety of techniques are available for DNA recombination in which adjoining ends of separate DNA fragments are tailored to facilitate ligation. Ligation refers to the formation of phosphodiester bonds between adjacent nucleotides, most often through the agency of the enzyme T4 DNA ligase. Thus, blunt ends may be directly ligated. Alternatively, fragments containing single strands at their adjoining ends that will bond to complementary single strands by hydrogen bonding can be ligated. Such single strands, referred to as cohesive termini, can be formed by the addition of nucleotides to blunt ends using terminal transferase. However, restriction endonucleases are most commonly used to produce cohesive termini. These enzymes cleave phosphodiester bonds in and around unique sequences of nucleotides of about 4–6 base pairs in length. Many restriction endonucleases and their recognition sites are known, the so-called Eco RI endonuclease being the most widely known. Typically, a plasmid or other cloning vehicle is cleaved, leaving termini each comprising half the restriction endonuclease recognition site, and a cleavage product of exogenous DNA obtained with the same restriction endonuclease having complementary ends is inserted into the cleaved vector. Many variations of these techniques are known to those skilled in the art and can be used in the practice of the present invention.

The exogenous, i.e., donor, DNA used in producing the gene library of the present invention is obtained from suitable cells of a donor identified as described above. When a cDNA donor gene library is being produced, it is preferred to use cells obtained from an organ of the mDNA donor that is the same as the organ attacked by the autoimmune disease in the host. For example, if an autoimmune disease attacks the liver of a host, liver cells from the donor are preferred since cells of different organs are more likely to express peptides which are not reactive with the autoantibody against which protection is desired. When cDNA fragments are being prepared, messenger DNA is obtained from the donor cells by any of the various techniques which exist for this purpose.

For example, the following method can be used to isolate messenger RNA from any mammalian tissue or cell culture that can be dispersed into single cells. A more detailed description of this technique is given in Maniatis et al, *Molecular Cloning: a laboratory manual*, Cold Spring Harbor Laboratory, Cold Spring Harbor, N.Y., 1982, pages 191–199, which is herein incorporated by reference. Cells are separated from the culture medium and washed in phosphate-buffered saline. The cells are then centifuged to remove the supernatant and resuspended in a lysis buffer containing approximately 1,000 units/ml RNasin or 10 mN vanadyl-ribonucleotide complexes. After mixing, storing, and centrifuging on a gradient, the cytoplasmic layer is recovered and added to a buffer containing a denaturing agent. A proteinase is then added to destroy protein. Proteins are removed by extracting once with phenol/chloroform. The aqueous phase is recovered and stored after ethanol has been added. The stored solution is then centrifuged to obtain a pellet containing nucleic acids. The nucleic acids are redissolved in a small volume of buffer containing RNasin or vanadyl-ribonucleoside complexes. A DNase is added to destroy DNA. After incubation, the resulting material is extracted once with phenol/chloroform. A solution of sodium acetate is added and the nucleic acids are precipitated with ethanol. Precipitated RNA is stored in aqueous ethanol at −70° C. As alternatives, the guanidinium/hot phenol method and the guanidinium/cesium chloride method may be used. Both of these techniques are described in the Maniatis et al publication cited above. If desired, polyadenylated RNA can be separated from nonpolyadenylated RNAs. The method of choice is chromatography on oligo (dT)-cellulose, which can be prepared in the laboratory or obtained commercially. A detailed technique for selection of polyadenylated RNA is set forth in the Maniatis et al publication cited above.

Complementary DNA is then produced from the isolated mRNA by the enzyme reverse transcriptase. The resulting single-stranded DNA is converted into double-stranded DNA using DNA polymerase. When cDNA is produced in this manner from all the mRNA that is present in a cell and is inserted into a cloning vehicle, the resulting collection of cDNA is referred to as a "donor gene library" since it contains DNA sequences coding for the gene products of the donor that were being expressed at the time the orginal mRNA was collected.

It should be noted that the production of a donor gene library by itself is well known and that this discussion of producing a donor library is merely to point out the nature of the biochemical reactions that are carried out in the practice of the present invention. The invention does not depend on the existence of a particular gene library but can use any gene library, whether compiled specifically for the purpose of this invention or for any other purpose, that meets the requirements set forth in this specification.

The vector used in the production of the host gene library can be any vector that replicates in a unicellular organism. For example, many plasmids suitable for use in the practice of this invention have been described in recent U.S. patents such as U.S. Pat. Nos. 4,273,875; 4,304,863; 4,419,450: 4,403,036; 4,363,877: 4,356,270: 4,349,629; and 4,332,901. Other vectors suitable for use in the practice of this invention include pAJ 655 (host bacteria, *E. Coli* FERMBP 136), pAJ 611 (host bacteria, *E. Coli* FERM-BP 138), pAJ 440 (host bacteria, Bacillus Subtilis ATCC 391391), pAJ 1844 (host bacteria, *E. Coli* FERM-BP 137), and pAJ 3148 (host bacteria, *Corynebacterium glutamicum* ATCC 39137). Particularly preferred is the phage vector λgtll which can be produced from publically available phages according to the procedure described in Young et al, Proc. Natl. Acad. Sci. USA 80 1194–1198 (1983). Briefly, this preferred phage vector can be produced as follows:

λgt7-lac5 and λ540 (ΔB imm21 nin5) are cleaved with HindIII, and the fragments are pooled and then ligated with T4 DNA ligase. The desired phage recombinant produces turbid (imm21) blue (lac5) plaques when the DNA is transfected into *E. coli* BNN93 and cells are plated on medium containing the chromogenic indicator 5-bromo-4-chloro-3-indolyl β- D-galactoside (X-Gal). The λgt7-lac5-λ540 hybrid is then crossed with λgt4 (c1857 S100 nin5) and recombinants, grown at 42° C., are scored for the formation of clear (c1857) blue plagues on X-Gal plates. The presence of the amber mutation S100 is confirmed by examining relative plating efficiency on hosts that contain or lack the amber suppressor supF (BNN45 or BNN93, respectively). Finally, the lac5 c1857 S100 phage is mapped for EcoRI cleavage sites. The phage λgtll contains a single EcoRI cleavage site.

Once a donor gene library is available, either according to the procedures described above or by any other procedure, recipient cells are transformed with the gene library to produce a series of transformed. cells containing the various donor DNA (or cDNA) fragments. The incorporation of the recombinant DNA into recipient cells can be accomplished by treating the recipient unicellular microorganisms with calcium chloride to increase the permeability of the cell membranes to DNA, as is reported in Mandel et al, *J. Mol. Biol.*, 53 159 (1970). Other methods for transforming recipient cells include incorporating the recombinant DNA at a stage of growth when cells become capable of incorporating DNA (the so-called competent cell stage) as is reported in Young et al, Gene, 1, 153 (1977). Plasmids can also be incorporated into DNA recipients by forming protoplasts or spheroplasts of the DNA recipients (particularly used for yeast), as described in Chang et al, *Mol. Ec. Gen. Genet.*, 168, 111 (1979). Any other method of transforming recipient cells can be used in the practice of this aspect of the invention.

Autoimmune antigens can be obtained from recipient cells using any of a multitude of known techniques. For example, cells that express peptide antigens in a manner such that the antigens are transported through the cell membrane into the surrounding space can be grown in a culture medium, and the desired antigen can be obtained directly from the medium. If the desired antigen is retained inside the cell membrane, cells can be lysed to release the antigen into the cell supernatant, which can then be purified to obtain the desired antigen. If the antigen being produced has an adverse effect on the cell expressing the antigen, placing the gene for the antigen under the control of an inducer allows expression of the gene only at the time of collection. For example, a λ phage can be grown on cells containing pNC9, a PBR322 derivative containing laci$^Q$. Sufficient lac repressor is produced in the cells to repress expression of the hybrid protein during phage lytic growth. Expression of the hybrid can be induced in infected cells with IPTG, and the antigen so produced is released from the cells upon cell lysis.

When the λgtll phage is used in one of the preferred aspects of the invention, the following procedure is preferred for screening with antibodies to determine the presence of autoimmune antigens. A recommended host is *E. coli* Y1090, which is ΔlacU169 proA$^+$ Δlon araD139 strA supF [trpC22::Tn10] (pMC9). The host bacterium is infected and plated in soft agar, after which the plate is incubated for approximately 5 hours at about 42{C. For even distribution of phages, approximately 104 phages per small plate and 105 phages per large plate is recommended. The plate is overlayed with a dry nitrocellulose filtered disk, previously soaked in 10 mM IPTG. The plate is incubated at approximately 37{C. The filter is then removed and washed in trisbuffered saline, pH 8.1 at room temperature for approximately 5–10 minutes. The filter is then incubated in TBS containing about 20% fetal calf serum (or 3% BSA or Ovalbumin). Incubation is for approximately 30 minutes at room temperature. The filter is then incubated in TBS +20% fetal calf serum plus antibody (approximately a 1:1 dilution of serum or IgG; if IgG is used, IgG is initially present at 10 mg/ml). Incubation occurs for approximately one hour at room temperature. The filter is then washed to remove unbound antibody and incubated in TBS containing $^{125}$I-protein A (approximately $10^6$ cpn/filter) for about one hour at room temperature. Radioactivity will be present at locations where antibody binding indicated the presence of expressed antigen.

Although this technique represents a preferred embodiment of the invention, other methods of screening with antibody probes are known to those skilled in the art and can readily be used in place of this technique.

The word "transformant" is used in this application in its broadest sense to refer to any recipient cell which has exogenous genetic information inserted therein. In addition to the more restricted meaning of transformant (a cell which has incorporated an plasmid), transformant in this application refers to cells which have exogenous DNA inserted into their chromosome (or chromosomes) as well as to cells which contain any recombinant vector as described above.

The plural recipient cells which are transformed using a donor gene library are referred to as expression libraries since the transformants will express gene products from the recombinant DNA vectors that have been randomly inserted into the individual unicellular organisms. Typically, the transformants are cloned to produce a series of cell lines arising from individual original transformants. A sample is selected from each cell line and (after lysing if desired) is exposed to the autoantibody associated with the immune disease in the host prepared as described above. Binding interactions between the autoantibody and the antigen expressed by the transformant containing the proper gene can be detected by any of the various methods available for this process. For example, proteins from colonies of transformants can be adsorbed onto nitrocellulose filter paper overlayed on the colonies followed by addition of the autoimmune antibody, washing to remove unreacted antibody, and detecting protein-bound antibody with radioactively labeled protein A. Cell colonies identified in this manner can be grown in large quantity to provide the desired amount of the gene coding for the protein antigen. At this point, several variations are possible. The cells containing the gene for the protein antigen can be allowed to express the antigen and the antigen can be recovered from the culture medium using known techniques. Alternatively, the donor cDNA fragment can be exised from the first vector and (e.g., by excession with the same endonuclease used to cleave the plasmid and insert the DNA originally), inserted into a new cloning vector, and used to transform a recipient cell for a large scale production of the cDNA or the protein antigen. Alternatively, it is also possible, once relatively large quantities of the protein antigen or the cDNA which produces it are available, to determine the sequence of the molecular species. Once this sequence is known, it is possible to synthesize the peptide antigen using an automated peptide synthesizer or other suitable means of synthesis. Both laboratory techniques of synthesis, typically solid-phase synthesis, and automated peptide synthesizers are well known in the art. See, for example, page 34 of the November/December 1984 issue of Genetic Engineering News, which contains a commercial advertisement for such equipment. Since a given DNA sequence will code for a single peptide, the genetic information present in the cloned DNA segment can readily be used in a non-biological synthesis of a peptide. Since hydrophobic regions of a peptide are generally on the interior of the peptide and hydrophilic regions are generally on the exterior, it is possible to predict with reasonable certainty those portions of the peptide that will be on the exterior surfaces and therefore available to act as antigenic determinants. Hydrophilicity analysis using the method of Hopp and Woods, *Proc. Natl. Acad. Sci. USA*, 78, 3824–3828 (1981), can be used to identify regions of peptides having high hydrophilicity. Antigenic determinants often have a sequence of 3–10 amino acids with higher than average hydrophilicity values. Artificial peptides produced using the genetic information preferably contain the entire hydrophilic region as described above. More preferably, artificial peptides have a sequence sufficiently identical to the sequence coded by the cloned DNA segment to make the antigenic determinant available for reaction with the autoantibody. An identical sequence is most preferred, but it will be readily recognized by those skilled in the art that minor modifications in the protein structure can be made without affecting the antigenic determinant. For example, substitution of closely related amino acids (leucine for isoleucine) and production of peptides with substituted (e.g., cysteine) or missing terminal amino acids (preferably no more than 10 percent of the total amino acid content) are both possible.

Other typical modifications include addition of different amino acids to allow coupling of the antigen to various surfaces. For example, addition or substitution of a cysteine allows attachment of the sulfhydryl group to a functionalized surface and addition or substitution of hydrophobic amino acids allows attachment by hydrophobic bonding to plastic surfaces. Both of these methods can be used, for example, in ELISA assays and other standard immunoassays. Modifications which fall within the scope of the present invention can readily be determined by their ability to react with the autoimmune antibody.

Any of these or other equivalent methods are suitable for obtaining an antigen which is reactive with the autoantibody associated with the autoimmune disease of the host from which serum was originally obtained.

In addition to the above general procedures which can be used for preparing recombinant DNA molecules and transformed unicellular organisms in accordance with the practices of this invention, other known techniques and modificatons thereof can be used in carrying out the practice of the invention. In particular, techniques relating to genetic engineering have recently undergone explosive growth and development. Many recent U.S. patents disclose plasmids, genetically engineered microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA.

All of these patents as well as all other patents and other publications cited in this disclosure are indicative of the level of skill of those skilled in the art to which this invention pertains and are all herein incorporated by reference.

Although some of these patents are directed to the production of a particular gene product that is not within the scope of the present invention, the procedures described therein can easily be modified to the practice of the invention described in this specification by those skilled in the art of genetic engineering. For example, the production of fused proteins can provide increased protein and antigenic stability, which is useful in the practice of the described invention. Antigens reactive with autoantibodies are normal host constituents and are especially susceptible to degradation. For long-term storage in diagnostic and large-volume exposure in therapeutic aspects of this invention, enhanced stability is desired. In addition, for a variety of different antigenic materials to be applied in a common diagnostic or therapeutic device, a common fused protein moiety (e.g., β-galactosidase) can enhance the flexibility of the method.

Although the method of the invention can be used in the treatment of any autoimmune disease, it is particularly preferred for use in SLE and associated autoimmune disorders such as scleroderma, sicca syndrome, mixed connective tissue disease (MCTD), and Sjogren's syndrome.

Antigens identified and produced by the method of the present invention have many uses, for example in the identification and treatment of autoimmune disorders. In many autoimmune disorders, symptoms are alleviated by removal of autoantibodies from the afflicted human or animal. Selective removal is desired so that the afflicted host can still be able to exhibit normal immune responses to exogenous antigens. As discussed in Terman et al, *Clinical Immunoloby and Immunopathology*, 8, 90–96 (1977), removal of DNA antibodies in vivo has been accomplished by extracorporeal circulation of blood over DNA immobilized on charcoal. This technique can easily be adapted for use with autoimmune diseases involving protein antigens by replacing the DNA immobilized on charcoal by appropriate protein antigens produced as described herein immobilized on a suitable substrate. Another example of a method and an apparatus for treatment of autoimmune diseases is set forth in U.S. Pat. No. 4,362,155. This patent discloses removing interferon and/or autoantibodies from blood. The method and apparatus can be readily adapted to use the antigens disclosed in the present invention instead of the general adsorbants disclosed in the patent.

The purified antigens that are reactive with patient autoantibodies can be attached to solid matrices and used to deplete, trap, or otherwise remove the reactive autoantibodies from the plasma of inflicted hosts. Methods for attaching peptides to surfaces are well known and can readily be adapted for use with this invention. For example, a terminal amino acid of a peptide antigen can react with a reactive carbonyl, carboxylate, hydroxyl, or amino group of a solid polymer (or of a linking group attached to the polymer). Coating of unmodified peptide on plastic or glass surfaces can also be used to provide an immunologically reactive surface.

Patients with autoimmune diseases such as myesthenia gravis and systemic lupus as well as those with some forms of cancer have been successfully treated with subtractive therapies in which all antibodies are depleted from the blood of the patient. These methods have suffered from the non-availability of chemically pure, reactive antigens, the method described herein provides for the first time large amounts of antigenic proteins that can be used to deplete the host plasma of specific autoantibodies. Thus, in practice, the beneficial antibodies can be returned to the host, thus avoiding the use of expensive and potentially complicating replacement fluids (e.g., albumin).

For example, patients with SLE or Sjorgen's syndrome that produce autoantibodies that react with the La protein can encounter a crisis of cellular destruction and inflammation. Such a patient can be treated by circulation or percolation of her serum through an apheresis device in which genetically produced La protein has been incorporated at high concentrations. The device can be designed such that every potential La autoantibody is disposed to an immobilized La antigen. The antigen can be attached to the solid matrix by means of a protein portion that has been genetically fused and expressed (e.g., β-galactosidase or a strong matrix binding protein such as avidin). Attachment by means of a fused handle, arm, or tag will have the advantages of (1) allowing a common chemical attachment source so that various antigens can be identically conjugated to a common matrix, (2) allowing maximum freedom of mobility of the antigen, a quality that is known to improve antibody antigen reactivity, and (3) providing for enhanced stability of the antigen. The resultant subtraction of La autoantibodies from the patient's blood will prevent or alter the ability of immuno complexes to form, and deposition of complexes in inflammed tissues of a patient can be reduced. The initial step in this procedure requires the subtraction of preformed La immune complexes using crude plasmapheresis or immunoglobulin depletion with staph protein A followed by specific depletion of the newly produced La autoantibodies before they can encounter antigens in the host with which to react. Thus, the blood of the patient could then remain free of immune complexes containing the La antigen.

Protein antigens produced according to the invention could also be used by direct injection of the antigen into the afflicted host in order to perturb the formation of immune complexes. Immune complexes that form as a result of autoimmunity depend upon the presence of critical concentrations of the reactants (antigen and antibody), and the ratio of the reactants one to another determines whether binding will occur. This ratio is presumed to be optimal during periods of crisis in the autoimmune disease state. By the method of the present invention, homogeneously pure antigens can be injected into the blood of the host and thus alter the antigen-antibody ratio. The resultant failure to form new immune complexes will allow the reticuloendothelial system and phagocytes to successfully remove preformed immune complexes, thus diminishing the ability of the immune complexes to deposit in target tissues where they are associated with autoimmune pathology.

For example, purified La antigen can be injected intervenously into a patient who is producing La autoantibodies during a life threatening autoimmune crises in which immune complexes with La antigen are forming more rapidly than they can be cleared and destroyed. In an average human host of 68 kg weight with 4.8 liters of whole blood, there are about $5 \times 10^4$ mm of IgG. In typical patients with circulating La autoantibodies, this represents an approximate equivalence of $10^{15}$ molecules of La antibody in total. Thus, injection of a molar equivalence of La antigen (approximately 1.6 nanomoles) would prevent formation of immune complexes that optimally result during states of high antibody-low antigen ratios. The current hypothesis of autoimmunity based upon formation of pathogenic immune complexes at the site of deposit rather than in free circulation maintains that the presence of a high-affinity antigen in circulation should decrease the rate of deposit of immune complexes in target tissues. In order to properly determine the quantity of circulating autoantibodies, the quantitative diagnostic methods described in the present invention can be applied, and the quantity of purified antigen injected can be adjusted accordingly as the level of autoantibodies rises or falls.

The present invention also relates to the development of a new approach to the diagnosis and classification of autoimmune diseases based upon the isolation of recombinant DNAs that encode the human antigens. The isolation and cloning procedure has been used to produce several antigens.

For example, the four chief autoimmune antigens La, Ro, Sm and RNP constitute the majority of such patients. La and Ro indicate Sjogren's syndrome and Ro is singly the most common of all of the autoantigens. Anti U1 RNP is an absolute marker for mixed connective tissue disease and Sm shows a strong SLE association with some overlap across several of the autoimmune disease categories.

Scleroderma-70 is reactive with human topoisomerase I and together with the centromeric and nucleolar antigens are diagnostic for scleroderma, another autoimmune disease with particular symptoms and prognosis. The development of scl-70 antibodies is the strongest diagnostic feature of peripheral scleroderma.

The other autoantigens such as U2 RNP, ribosomal RNP, RNA, etc. have various degrees of occurrence and are appearing to be more common than previously suspected based upon these more sensitive tests.

The sequences of some of the antigens provided by this invention are provided below. Proteins having these sequences can be used in accordance with the present invention, but longer proteins containing the antigens of the present invention bound to an inert carrier can of course be used. For example any of these proteins can be attached to various polymeric materials known in this art. Such polymeric materials include any polyamino acid sequence known in the art, e.g., polylysine. Other biological or non-biological materials can also be used. For example, the proteins of this invention can be linked to human or bovine serum albumin, thyroglobulin, ovalbumin, or keyhole limpet hemocyanin, or palmitic acid. Other carriers which can be used include dextrans, e.g., sepharose.

The ability to produce the purified antigens by recombinant DNA procedures using prototype patient antibodies to screen cDNA expression libraries has made such tests available for the first time. This new testing procedure should result in a new view of each patient as defined by a spectrum of autoantibody systems rather than by gross categorization by fluorescence.

Below, is described the autoimmune dipstick that includes several purified autoantigens, some produced by molecular cloning and others produced by standard isolation procedures (e.g. histones, DNA, RNA). The dipstick is a qualitative determination for general use in clinics and physician's offices. It is backed by a quantitative ELISA test using microtiter plates that will allow precise numerical assignments of each patient's spectrum of autoantibody systems. It is anticipated that in the long term, the knowledge gained through this precise procedure will result in a new kind of categorization and predicted prognosis. Thus, the present system of disease assignments may become obsolete because the sensitivity and accuracy of diagnosis will be drastically improved.

Using a simple 2 hour centrifugation procedure, fusion proteins between β-galactosidase and each human autoantigen are purified and placed on nitrocellulose strips. The strips containing each of the purified antigens are then reacted with the blood of a patient suspected of having disease. The spectrum of reactivity among a group of 10 to 15 antigens will allow a rapid categorization of autoantibody systems that are characteristic of autoimmune diseases (see Table 1 below).

tration only and are not intended to be limiting of the invention or any embodiment thereof, unless specified.

Results:

(1) La: The La protein that is diagnostic for Sjogren's syndrome but also occurs in systemic lupus erythematosus is the model antigen around which the method of the above-identified application has been developed and advanced. cDNA has been isolated from a human liver library using a prototype patient's serum. Large amounts of the fusion protein have been expressed and purified using *E. coli*. The fusion protein produces a strong and sensitive signal for diagnosis of other La reactive patient antisera (Chambers and Keene, PNAS 82:2115–2119, 1985).

The amino acid sequence for La protein is presented below.

TABLE 1

Percent Occurrence of Autoantibodies Among Patients with Autoimmune Diseases

| ANTIGEN | systemic lupus erythematosus SLE | mixed connective tissue disease MCTD | primary Sjogren's syndrome 1° SS | progressive systemic sclerosis PSS | myositis | congenital fetal heartblock |
|---|---|---|---|---|---|---|
| La | 9 | 3 | 40 | 1 | 0 | — |
| Ro | 25 | 20 | 75 | 4 | 8 | 85 |
| Sm | 25 | 7 | 0 | 0 | 0 | — |
| U1 RNP | 25 | 100 | 4 | 3 | 15 | — |
| Scl-70 | 0 | 0 | 0 | 20 | 0 | — |
| centromeric | 2 | 0 | 0 | 30 | 0 | — |
| nucleolar | 7 | 0 | 0 | 40 | 8 | — |
| Jo-1 | 0 | 0 | 0 | 0 | 25 | — |
| U2 RNP | * | * | * | * | * | * |
| ribosomal | 3 | 0 | 2 | 1 | 0 | — |
| DNA | 70 | 50 | 30 | 55 | 25 | — |

Values were averaged for several reports in the literature and were obtained by standard FANA tests, counterimmunoelectrophoresis, immunoprecipitation and immunoblotting.
(rheumatoid arthritis, discoid lupus, drug induced lupus are not shown)
*The asterisk indicates an undetermined value.

The invention now being generally described, the same will be better understood by reference to certain illustrative examples which are included herein for purposes of illus-

La (SS-B)

| | | | | | | | | | | | | | | | | | | |
|---|---|---|---|---|---|---|---|---|---|---|---|---|---|---|---|---|---|---|
| | | | | | | | | | Met | Ala | Glu | Asn | Gly | Asp | Asn | Glu | Lys |
| Met | Ala | Ala | Leu | Glu | Ala | Lys | Ile | Cys | His | Gln | Ile | Glu | Tyr | Tyr | Phe | Gly | Asp |
| Phe | Asn | Leu | Pro | Arg | Asp | Lys | Phe | Leu | Lys | Glu | Gln | Ile | Lys | Leu | Asp | Glu | Gly |
| Trp | Val | Pro | Leu | Glu | Ile | Met | Ile | Lys | Phe | Asn | Arg | Leu | Asn | Arg | Leu | Thr | Thr |
| Asp | Phe | Asn | Val | Ile | Val | Glu | Ala | Leu | Ser | Lys | Ser | Lys | Ala | Glu | Leu | Met | Glu |
| Ile | Ser | Glu | Asp | Lys | Thr | Lys | Ile | Arg | Arg | Ser | Pro | Ser | Lys | Pro | Leu | Pro | Glu |
| Val | Thr | Asp | Glu | Tyr | Lys | Asn | Asp | Val | Lys | Asn | Arg | Ser | Val | Tyr | Ile | Lys | Gly |
| Phe | Pro | Thr | Asp | Ala | Thr | Leu | Asp | Asp | Ile | Lys | Glu | Trp | Leu | Glu | Asp | Lys | Gly |
| Gln | Val | Leu | Asn | Ile | Gln | Met | Arg | Arg | Thr | Leu | His | Lys | Ala | Phe | Lys | Gly | Ser |
| Ile | Phe | Val | Val | Phe | Asp | Ser | Ile | Glu | Ser | Ala | Lys | Lys | Phe | Val | Glu | Thr | Pro |
| Gly | Gln | Lys | Tyr | Lys | Glu | Thr | Asp | Leu | Leu | Ile | Leu | Phe | Lys | Asp | Asp | Tyr | Phe |
| Ala | Lys | Lys | Asn | Glu | Glu | Arg | Lys | Gln | Asn | Lys | Val | Glu | Ala | Lys | Leu | Arg | Ala |
| Lys | Gln | Glu | Gln | Glu | Ala | Lys | Gln | Lys | Leu | Glu | Glu | Asp | Ala | Glu | Met | Lys | Ser |
| Leu | Glu | Glu | Lys | Ile | Gly | Cys | Leu | Leu | Lys | Phe | Ser | Gly | Asp | Leu | Asp | Asp | Gln |
| Thr | Cys | Arg | Glu | Asp | Leu | His | Ile | Leu | Phe | Ser | Asn | His | Gly | Glu | Ile | Lys | Trp |
| Ile | Asp | Phe | Val | Arg | Gly | Ala | Lys | Glu | Gly | Ile | Ile | Leu | Phe | Lys | Glu | Lys | Ala |
| Lys | Glu | Ala | Leu | Gly | Lys | Ala | Lys | Asp | Ala | Asn | Asn | Gly | Asn | Leu | Gln | Leu | Arg |
| Asn | Lys | Glu | Val | Thr | Trp | Glu | Val | Leu | Glu | Gly | Glu | Val | Glu | Lys | Glu | Ala | Leu |
| Lys | Lys | Ile | Ile | Glu | Asp | Gln | Gln | Glu | Ser | Leu | Asn | Lys | Trp | Lys | Ser | Lys | Gly |
| Arg | Arg | Phe | Lys | Gly | Lys | Gly | Lys | Gly | Asn | Lys | Ala | Ala | Gln | Pro | Gly | Ser | Gly |
| Lys | Gly | Lys | Val | Gln | Phe | Gln | Gly | Lys | Lys | Thr | Lys | Phe | Ala | Ser | Asp | Asp | Glu |
| His | Asp | Glu | His | Asp | Glu | Asn | Gly | Ala | Thr | Gly | Pro | Val | Lys | Arg | Ala | Arg | Glu |
| Glu | Thr | Asp | Lys | Glu | Glu | Pro | Ala | Ser | Lys | Gln | Gln | Lys | Thr | Glu | Asn | Gly | Ala |
| Gly | Asp | Gln | | | | | | | | | | | | | | | |

(2) Ro: La protein is clinically related to the protein Ro that is highly common among autoimmune patients. Ro is characteristic of patients with Sjogren's syndrome and is likely to be a major pathogenic factor in the fetal heartblock syndrome. La and Ro proteins sometimes reside on the same cellular ribonucleoprotein particle and the antibody systems tend to occur together. Most La patients contain some Ro antibodies and vice versa. cDNA encoding the Ro protein has been isolated from a human brain library and expressed in *E. coli* as a fusion protein. The purified fusion protein has been incorporated into our assay.

The amino acid sequence for the major antigenic portion of Ro protein is presented below.

above-identified application to express and purify large amounts of the fusion protein from *E. coli*.

The majority of the amino acid sequence that encodes this antigen is shown below.

Ro (SS-A)

| | | | | | | | | | | | | | | | | | | |
|---|---|---|---|---|---|---|---|---|---|---|---|---|---|---|---|---|---|---|
| Val | Gln | Val | Arg | Phe | Pro | Gly | Thr | Ser | Pro | Ala | Pro | Leu | Leu | Leu | Pro | Arg | Leu | Arg | Pro |
| Arg | Gly | Arg | Leu | Pro | Gly | Thr | Gly | Leu | Ala | Ile | Val | Thr | Lys | Tyr | Ile | Thr | Lys | Gly | Trp |
| Lys | Glu | Val | His | Glu | Leu | Tyr | Lys | Glu | Lys | Ala | Leu | Ser | Val | Glu | Thr | Glu | Lys | Leu | Leu |
| Lys | Tyr | Leu | Glu | Ala | Val | Glu | Lys | Val | Lys | Arg | Thr | Lys | Asp | Glu | Leu | Glu | Val | Ile | His |
| Leu | Ile | Glu | Glu | His | Arg | Leu | Val | Arg | Glu | His | Leu | Leu | Thr | Asn | His | Leu | Lys | Ser | Lys |
| Glu | Val | Trp | Lys | Ala | Leu | Leu | Gln | Glu | Met | Pro | Leu | Thr | Ala | Leu | Leu | Arg | Asn | Leu | Gly |
| Lys | Met | Thr | Ala | Asn | Ser | Val | Leu | Glu | Pro | Gly | Asn | Ser | Glu | Val | Ser | Leu | Val | Cys | Glu |
| Lys | Leu | Cys | Asn | Glu | Lys | Leu | Leu | Lys | Lys | Ala | Arg | Ile | His | Pro | Phe | His | Ile | Leu | Ile |
| Ala | Leu | Glu | Thr | Tyr | Lys | Thr | Gly | His | Gly | Leu | Arg | Gly | Lys | Leu | Lys | Trp | Arg | Pro | Asp |
| Glu | Glu | Ile | Leu | Lys | Ala | Leu | Asp | Ala | Ala | Phe | Tyr | Lys | Thr | Phe | Lys | Thr | Val | Glu | Pro |
| Thr | Gly | Lys | Arg | Phe | Leu | Leu | Ala | Val | Asp | Val | Ser | Ala | Ser | Met | Asn | Gln | Arg | Val | Leu |
| Gly | Ser | Ile | Leu | Asn | Ala | Ser | Thr | Val | Ala | Ala | Ala | Met | Cys | Met | Val | Val | Thr | Arg | Thr |
| Glu | Lys | Asp | Ser | Tyr | Val | Val | Ala | Phe | Ser | Asp | Glu | Met | Val | Pro | Cys | Pro | Val | Thr | Thr |
| Asp | Met | Thr | Leu | Gln | Gln | Val | Leu | Met | Ala | Met | Ser | Gln | Ile | Pro | Ala | Gly | Gly | Thr | Asp |
| Cys | Ser | Leu | Pro | Met | Ile | Trp | Ala | Gln | Lys | Thr | Asn | Thr | Pro | Ala | Asp | Val | Phe | Ile | Val |
| Phe | Thr | Asp | Asn | Glu | Thr | Phe | Ala | Gly | Gly | Val | His | Pro | Ala | Ile | Ala | Leu | Arg | Glu | Tyr |
| Arg | Lys | Lys | Met | Asp | Ile | Pro | Ala | Lys | Leu | Ile | Val | Cys | Gly | Met | Thr | Ser | Asn | Gly | Phe |
| Thr | Ile | Ala | Asp | Pro | Asp | Asp | Arg | Gly | Met | Leu | Asp | Met | Cys | Gly | Phe | Asp | Thr | Gly | Ala |
| Leu | Asp | Val | Ile | Arg | Asn | Phe | Thr | Leu | Asp | Met | Ile | End | Pro | End | Ala | Ala | Ala | Arg | Ser |
| Arg | Asp | Pro | Leu | Pro | Val | Ile | Ser | Leu | Lys | Asn | Ile | Gln | Leu | Leu | Pro | Ser | End | Ser |
| Pro | Pro | Asn | Glu | End | End | Trp | Tyr | Ser | Met | Cys | Ile | Met | | | | | | |

(3) U1-RNP: The U1 RNP antigen (U1 RNA bp or 68 K protein) is diagnostic of the mixed connective tissue diseases (MCTD) and has been isolated using the procedure of the

| U1-RNP |
| --- |
| (70K; 68K; anti-RNP) |

| | | | | | | | | | | | | | | | | | | | |
|---|---|---|---|---|---|---|---|---|---|---|---|---|---|---|---|---|---|---|---|
| Asn | Gln | Pro | Tyr | Cys | Gly | Ile | Ala | Pro | Tyr | Ile | Arg | Glu | Phe | Glu | Asp | Pro | Arg | Asp | Ala |
| Pro | Pro | Pro | Thr | Arg | Ala | Glu | Thr | Arg | Glu | Glu | Arg | Met | Glu | Arg | Lys | Arg | Arg | Glu | Lys |
| Ile | Lys | Arg | Arg | Gln | Gln | Glu | Val | Glu | Thr | Glu | Leu | Lys | Met | Trp | Asp | Pro | His | Asn | Asp |
| Pro | Asn | Ala | Gln | Gly | Asp | Ala | Phe | Lys | Thr | Leu | Phe | Val | Ala | Arg | Val | Asn | Tyr | Asp | Thr |
| Thr | Glu | Ser | Lys | Leu | Arg | Arg | Glu | Phe | Glu | Val | Tyr | Gly | Pro | Ile | Lys | Arg | Ile | His | Met |
| Val | Tyr | Ser | Lys | Arg | Ser | Gly | Lys | Pro | Arg | Gly | Tyr | Ala | Phe | Ile | Glu | Tyr | Glu | His | Glu |
| Arg | Asp | Met | His | Ser | Ala | Tyr | Lys | His | Ala | Asp | Gly | Lys | Lys | Ile | Asp | Gly | Arg | Arg | Val |
| Leu | Val | Asp | Val | Glu | Arg | Gly | Arg | Thr | Val | Lys | Gly | Trp | Arg | Pro | Arg | Arg | Leu | Gly | Gly |
| Gly | Leu | Gly | Gly | Thr | Arg | Arg | Gly | Gly | Ala | Asp | Val | Asn | Ile | Arg | His | Ser | Gly | Arg | Asp |
| Asp | Thr | Pro | | | | | | | | | | | | | | | | | |

The sequence of a much larger protein which encompasses this amino acid sequence was published by *Theissen et al* in "The EMBO Journal" vol. 5, no.12, pp. 3209–3217 (1986). Theissen et al make no suggestion that their longer protein possesses any immunodiagnostic of therapeutic use.

This protein was cloned using a human brain stem cDNA library and antibodies from a patient with MCTD.

(4) U2-RNP: The U2 RNP antigen (U2 RNA bp or A') is relatively rare among autoimmune patients but is frequently associated with a severe polymyositis-scleroderma overlap syndrome. This antigen was cloned using serum from one patient and a human liver cDNA library. This antigen is reactive with approximately 5–10% of tested patient sera.

The sequence of this protein is provided below.

Partial peptide sequences for these proteins in Artemia and human were published by Elkon et al in *Pro. Natl. Acad. Sci. USA*, Vol. 83, pp. 7419–7423, October 1986.

(6) Scl-70: The most prognostic autoantigenic protein for peripheral scleroderma is known as scl-70 to denote a protein of 70 Kd MW. This is more recently known to be 100 Kd and is human topoisomerase I. Scl-70 was cloned as cDNA from a human basal ganglia library using an experimental protocol which was analogous to the protocol used for the other antigens.

Sequences for topoisomerase I of yeast and Drosophila have been reported.

(7) Sm: The Smith antigen (Sm) is common in autoimmune patients but correlates with several distinct diseases. Biochemically confirmed Sm antigens have not yet been

| U2-RNP |
| --- |
| (A'; U2 RNA bp) |

| | | | | | | | | | | | | | | | |
|---|---|---|---|---|---|---|---|---|---|---|---|---|---|---|---|
| | | | | | | | | | | | Tyr | Lys | Ile | Pro | Val |
| Ile | Glu | Asn | Leu | Gly | Ala | Thr | Leu | Asp | Gln | Phe | Asp | Ala | Ile | Asp | Phe |
| Ser | Asp | Asn | Glu | Ile | Arg | Lys | Leu | Asp | Gly | Phe | Pro | Leu | Leu | Arg | Arg |
| Leu | Lys | Thr | Leu | Leu | Val | Asn | Asn | Asn | Arg | Ile | Cys | Arg | Ile | Gly | Glu |
| Gly | Leu | Asp | Gln | Ala | Leu | Pro | Cys | Leu | Thr | Glu | Leu | Ile | Leu | Thr | Asn |
| Asn | Ser | Leu | Val | Glu | Leu | Gly | Asp | Leu | Asp | Pro | Leu | Ala | Ser | Leu | Lys |
| Ser | Leu | Thr | Tyr | Leu | Ser | Ile | Leu | Arg | Asn | Pro | Val | Thr | Asn | Lys | Lys |
| His | Tyr | Arg | Leu | Tyr | Val | Ile | Tyr | Lys | Val | Pro | Val | Val | Arg | Val | Leu |
| Asp | Phe | Gln | Lys | Val | Lys | Leu | Lys | Glu | Arg | Gln | Glu | Ala | Glu | Lys | Met |
| Phe | Lys | Gly | Lys | Arg | Gly | Ala | Gln | Leu | Ala | Lys | Asp | Ile | Ala | Arg | Arg |
| Ser | Lys | Thr | Phe | Asn | Pro | Gly | Ala | Gly | Leu | Pro | Thr | Asp | Lys | Lys | Lys |
| Gly | Gly | Pro | Ser | Pro | Gly | Asp | Val | Gln | Ala | Ile | Lys | Asn | Ala | Ile | Ala |
| Asn | Ala | Ser | Thr | Leu | Ala | Glu | Val | Glu | Arg | Leu | Lys | Gly | Leu | Leu | Gln |
| Ser | Gly | Gln | Ile | Pro | Gly | Arg | Glu | Arg | Arg | Ser | Gly | Pro | Thr | Asp | Asp |
| Gly | Glu | Glu | Glu | Met | Glu | Glu | Asp | Thr | Val | Thr | Asn | Gly | Ser | | |

(5) ribosomal RNP: This autoimmune antigen exists on three characteristic ribosomal proteins of 36 Kd, 15 Kd and 13 Kd. All three have been cloned and expressed for use in the autoimmune diagnostic tests described in our application. This is not a highly common autoimmune specificity but recent tests have found is to occur in up to 15% of all patients.

The sequence of ribosomal RNP is provided below.

obtained and expressed as cDNA for these diagnostic procedures. Candidate clones have been isolated and are currently being characterized. I expect that this autoimmune specificity will soon be in hand by using the procedures of the above-identified application, and will be incorporated into this diagnostic autoimmune test. Several other autoantigenic recombinants have been isolated and are being systematically analyzed and added to the collection. The

| Ribosomal RNP |
| --- |
| (P0, P1, P2; L42; EL12) |

| | | | | | | | | | | | Pro | Ser | Leu | Leu | Pro |
|---|---|---|---|---|---|---|---|---|---|---|---|---|---|---|---|
| Gln | Ala | Ser | Arg | Ala | Pro | Ala | Ala | Gly | Ser | Ala | Pro | Ala | Ala | Ala | Glu |
| Glu | Lys | Lys | Asp | Glu | Lys | Lys | Glu | Glu | Ser | Glu | Glu | Ser | Asp | Asp | Asp |
| Met | Gly | Phe | Gly | Leu | Phe | Asp*** | | | | | | | | | | goals for the optimization of the diagnostic tests as described in the application (and by Chambers and Keene, PNAs, 1985) are shown in Table 2 (below).

All of the above cDNA clones that have been authenticated using large numbers of patient sera have been expressed in high frequency lysogens in order to produce large amounts of the antigenic b-galactosidase fusion proteins. An exemplary procedure for rapid purification of the fusion proteins is outlined below.

PURIFICATION OF β-GALACTOSIDASE FUSION PROTEIN (LYSOGEN PREP)

1. Inoculate 10 ml. LB broth-AMP with E. coli lysogen (from a single isolated colony on a plate). Incubate overnight at 30° C.
2. Inoculate 250 ml. culture with overnight culture (2.5 ml) Grow at 30 C to OD600=0.5 approx 2.5 hours or 2–4 X lo 8 cells/ml.
3. Add IPTG to 3 mM final concentration and induce with a temperature shift to 42° C. for 10–15 minutes.
4. Shake at 38° C. for 1.5–2 hours.
5. Harvest cells for centrifugation for 10 minutes at 5 k GSA rotor.
6. Resuspend in 5 ml. SM (0.1M NaCl, 0.016M $MgSO_4$, 0.05M Tris pH 7.5, 0.01% gelatin)
7. Lyze the cells by freezing and thawing in the presence of protease inhibitors 110 ug/ml phenyl methylsulfonyl fluoride (PMSF), 1)M leupeptin, 1 μM pepstatin.
8. Thaw cell suspension.
9. Treat with DNAse I at 10 ug/ml final concentration in 1 m M $MgCl_2$, 28 mM B-ME for 10 minutes in ice.
10. Add 2 ml. of 50% Sucrose, 0.1 M NaCl, 0.01M tris pH 8, 1 mM EDTA and lysozyme 60 ug/ml.
11. Incubate on ice for 30 minutes.
12. Add 1 ml. 10% NP40 and 1 ml. 0.5M EDTA, leave on ice 15 minutes.
13. Add 1 ml. of 10% Zwittergent (Calbiochem) and sonicate 3 to 4 times, 10 second each.
14. Layer suspension on 40% sucrose cushion (10 ml. on Corex tube. Spin for 30 minutes at 13,000 xg (11K) HB4 rotor at 4 C.
15. Save pellet, resuspend in Laemlli protein buffer or 3M urea.

Figure 7A:
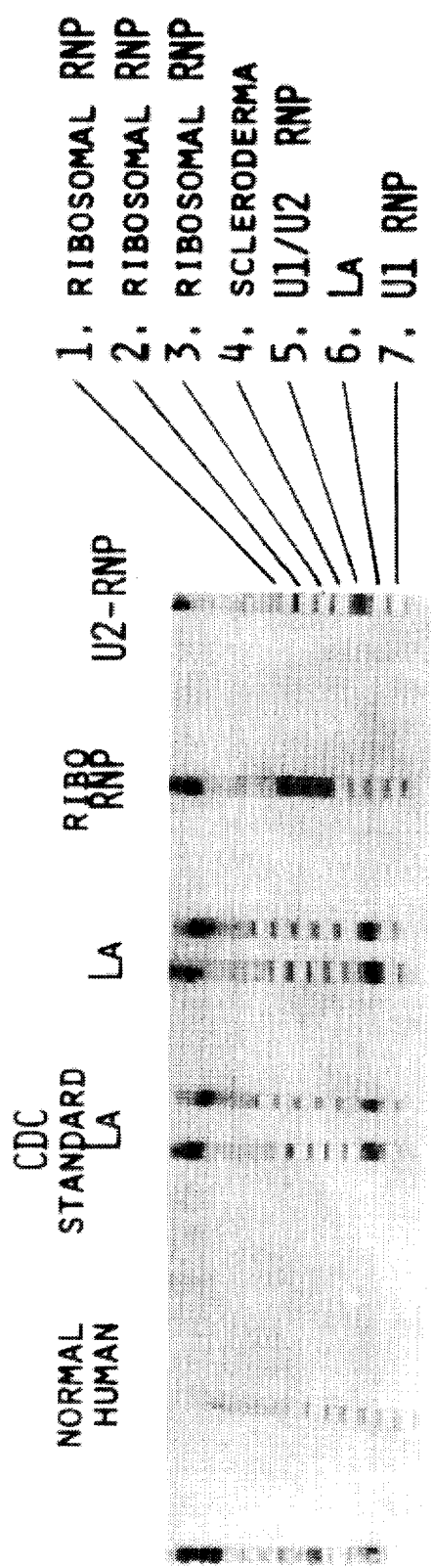
FIG. 7 illustrates an autoimmune dipstick provided by the present invention.
Figure 7B:
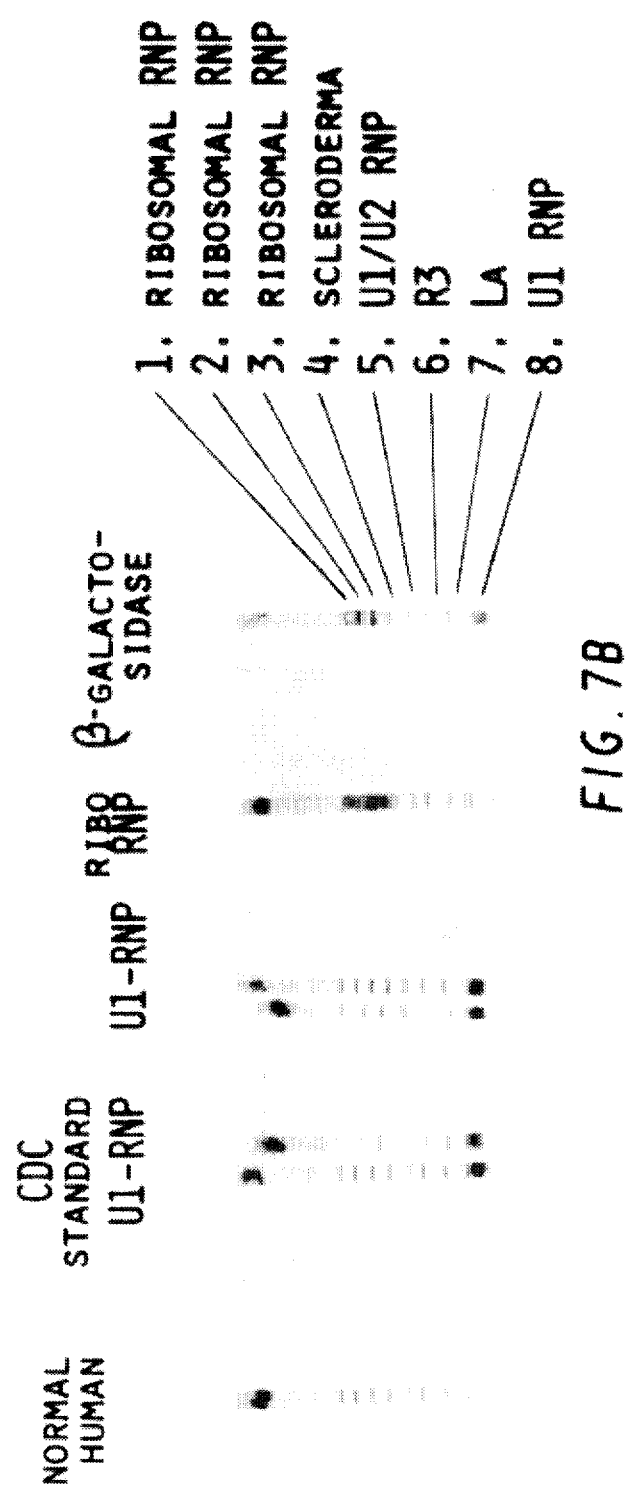

The procedure involves differential centrifugation of proteins from E. coli cell extracts infected with the lysogens. The procedure results in the rapid production of purified antigen because the fusion proteins are insoluble. The purified proteins are solubilized in solution of 3M to 6M urea and are immobolized onto nitrocellulose or plastic microtiter plates for ELISA testing of patient sera. Thus, these recombinantly produced antigens and several other autoreactive compounds have been collected and an autoimmune dipstick has been derived. An example of this device is shown in FIG. 7.

Figure 8:
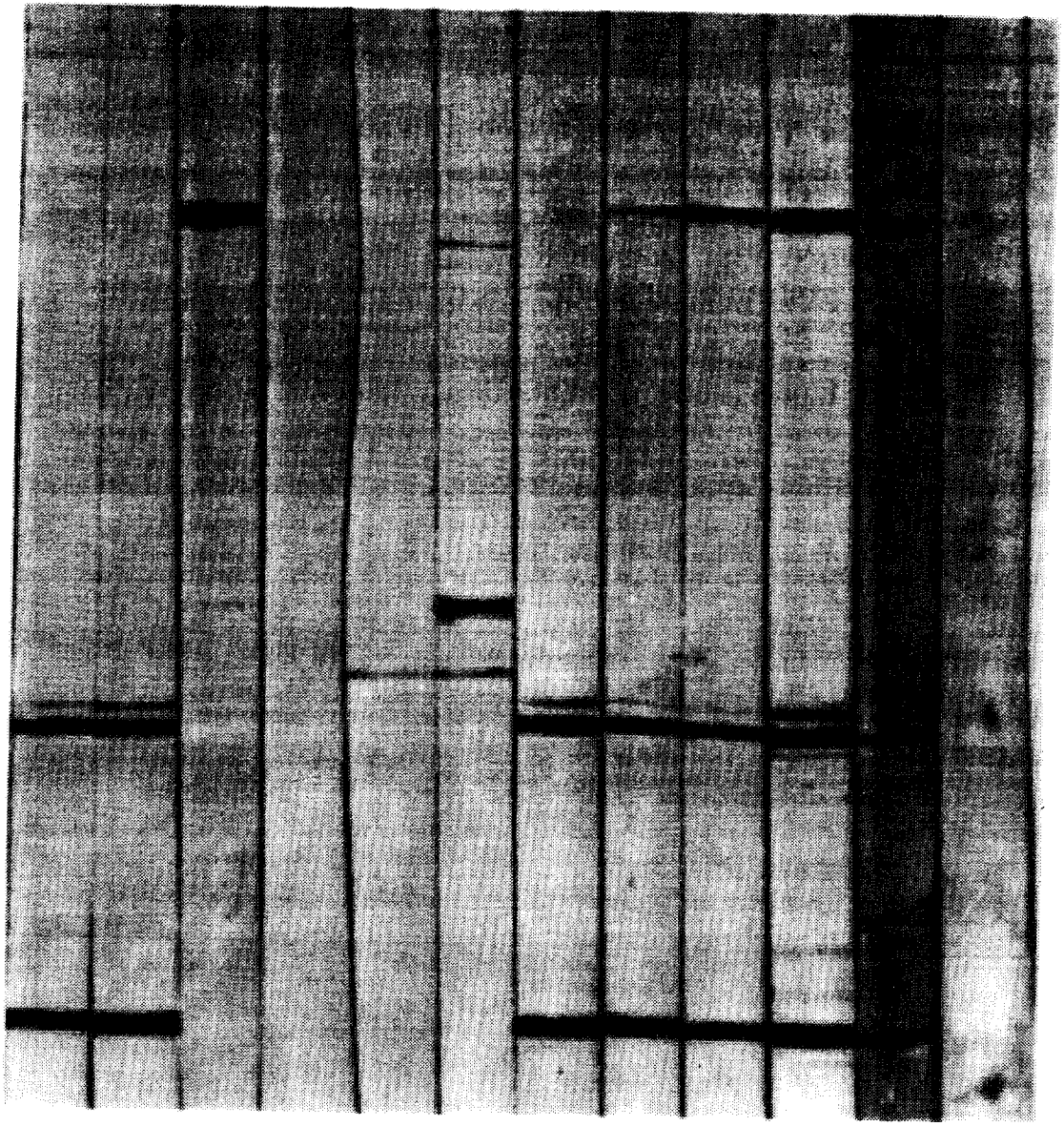
FIG. 8 illustrates an immunoblot showing reactivity of sera with autoantigens.

The procedures described involve the production of purified autoantigens from human tissues based upon identification of tissue reactivity using monospecific or approximately monospecific patient sera followed by screening of cDNA expression libraries representing those tissues. An example immunoblot showing reactivity of some sera with autoantigens is shown in FIG. 8. Lanes 3 and 5, for example, indicate human sera with strong single protein reactivities that have been used in our various procedures to identify the U1 RNP and U2 RNP antigens, respectively. The expressed antigens are authenticated, purified as β-galactosidase fusion proteins and adapted to a nitrocellulose immunoblot or microtiter ELISA. Sera from patients of unknown autoimmune reactivity are then tested against these recombinant antigens and classified according to the specificity of reactivity.

The dipstick ELISA gives qualitative assignments of autoimmune rectivity and approximates the category of disease readily. For example, La and/or Ro reactivity will indicate Sjogren's syndrome while U1 RNP will indicate mixed connective tissue disease and scl-70 will prognosticate peripheral scleroderma, etc. The autoimmune dipstick shown in Panel 8 is a prototype developed by use in 1985 that has been recently updated to include antigens produced by standard methods of purification in addition to the recombinantly produced proteins.

Table 2A below lists all of the antigens presently available and incorporated in the second generation autoimmune dipstick. The recombinantly produced antigens claimed under our application are indicated by an asterisk (*). Table 2B below indicates those antigens that will be adapted to the dipstick assay but that are not presently available in our research and development. The antigens summarized in Table 2 constitute the set needed to optimally put our technology into practice.

TABLE 2

| A | B |
|---|---|
| La* | Sm* |
| Ro* | centromere* |
| U1 RNP* | nucleolar* |
| U2 RNP* | rheumatoid factor |
| rRNP* | Epstein-Barr Virus Nuclear Antigen (EBNA) |
| scl-70* | other minor protein |
| histone | autoantigens* |
| ssDNA | related to those above* (A, B", B', B, C, D) |
| dsDNA | |
| tRNA* | |
| U1 RNA* | |
| tRNA his synthetase | |

Application of the same antigens in ELISAs using microtiter dishes is quantitative and will provide a precise classification of the patient's serum by percentage of reactivity with each autoantigen. This kind of precise numerical information has not been available previously and is likely to provide a profile of autoimmune reactivity that, together with clinical observations, will refine the definitions and categorizations of the autoimmune patient.

EXAMPLE

Isolation and Analysis of cDNA clones expressing the human lupus La antigen.

Introduction

The present invention has been reduced to practice and illustrated by the identification of recombinant cDNA clones made from human liver that express the La protein associated with systemic lupus erythematosus and Sjorgen's syndrome. Prior to the present invention there was no method known that would allow identification of the specific antigenic material, and only approximate assignment of antigenic specificities against standard prototype antisera was possible (1). The mammalian cell La protein was found associated with precursor forms of RNA polymerase III transcripts including tRNA, 4.5 S RNA, 5 S RNA, and 7–2 RNA (3,4,5,6). Some small vital transcripts such as VAI RNA of adenovirus (7,8), EBER RNAs of Epstein-Barr virus (9) and the leader RNAs of vesicular stomatitis virus (2,10) and rabies virus (11) were also shown to be complexed with the La protein. By immunoprecipitation of ribonucleoprotein complexes using La antibodies, the site of La protein binding to several of these RNA species was shown to reside near the 3' end (4,8,12). The presence of uridylate residues at the 3' ends of these RNAs may be required for binding. Furthermore, the addition of extra 3' terminal uridylate residues was found to enhance the binding of La protein to VAI RNA (13) and to transfer RNA (14). Because La protein preferentially binds to unprocessed transcripts, Steitz and coworkers (4,5) have proposed that La protein is a transcription factor for RNA polymerase III. Despite uncertainty regarding its exact function in RNA metabolism, it is clear that the La protein is biologically important in the regulation of gene expression because it associates with a variety of cellular and viral RNAs, many of which have known functions.

To further characterize the biochemical functions of the La protein, attempts have been made to purify it from mammalian cells (14). Recoveries from these purification procedures have been less than 7% and the La protein showed biochemical heterogeneity apparently due to interactions with RNA components. In order to produce large amounts of highly purified La protein, the inventors derived recombinant cDNA clones that code for La protein. La-cDNA colonies from λgt11 expression libraries (15) were identified using sera from selected lupus patients as antibody probes.

MATERIALS AND METHODS

Enzymes

Enzymes were purchased from Bethesda Research Laboratories and New England Biolabs. Rabbit reticulocyte lysate system for in vitro translation was from New England Nuclear.

Antisera

Lupus antisera were obtained from the Duke University Medical Center Fluorescent Antinuclear Antibody Laboratory. Sera that were strongly reactive with single specific antigens were identified and obtained in larger quantities by venipuncture.

Cells and Immunoprecipitation

HeLa cells were labeled in methionine-free medium for 5 h with [$^{35}$]-methionine (New England Nuclear) at 0.2–0.5 mCi/ml for antibody precipitations. Protein extracts were prepared and immunoprecipitations were carried out as described (8) using Pansorbin (Calbiochem) as a source of protein A. Immunoprecipitated proteins were analyzed by 15% SDS polyacrylamide gel electrophoresis (PAGE) (16) followed by fluorography.

Bacterial Strains and λgt11 expression libraries

E. coli strains Y1088 and Y1090 were obtained from D. Stafford (University of North Carolina at Chapel Hill). Human liver cDNA libraries constructed with λt11 were provided by D. Stafford and P. Modrich (Duke University Medical Center) and R. A. Lazzarini (National Institutes of Health).

Screening of expression libraries with antibody probes

As described by Young and Davis (15), λgt11 recombinant phages were plated on E. coli Y1090 at 105 pfu per 576 cm2 plate (NUCU Inter Med). Expression of β-galactosidase fusion proteins was induced by overlaying with nitrocellulose fibers (Schleicher and Schuell) that were saturated with 10 mM isopropyl thiogalactopyranoside (IPTG) (Boehringer Mannheim Biochemicals). Sera from lupus patients were screened by immunoprecipitation of r35S]-methionine-and [$^3$H]-amino-acid-labeled HeLa cell extracts to confirm the unique specificity of the autoantibodies or by immunoblotting using the technique of Towbin et al, Proc. Natl. Acad. Sci. USA, 76, 4350–4354 (1979). The La sera were determined to be free of Ro, Sm, RNP and other lupus autoantibodies prior to use in screening expression libraries. After transfer of induced proteins to nitrocellulose, the filters were blocked with fetal calf serum, screened with 1:100 dilutions of lupus antisera and probed with [$^{125}$I]-labeled protein A (ICN Radiochemicals).

Hybrid selection in the in vitro translation

The Eco RI-DNA inserts, recloned into pBR322, were immobilized on nitrocellulose filters and used for hybrid selection. Total HeLa cell cytoplasmic RNA was used in the hybrid selections as described by Maniatis et al (17). Hybrid selected mRNAs were translated in vitro using rabbit reticulocyte lysates in the presence of [$^{35}$S]-methionine and the products analyzed by 15% SDS/PAGE. Gel slices identified by autoradiography and containing the La protein were transferred to sample wells of a second gel. Varying amounts of S. aureus V8 protease (Sigma) were added to each well, and digestion was allowed to proceed in the stacking gel according to the method of Cleveland et al (18). The peptides generated by limited proteolysis were fractionated in the same gel and identified by fluorography.

DNA sequencing

Eco RI-inserts isolated from λgt11-LA clones were fragmented using restriction enzymes and subcloned into M13-mp18 and M13-mp19 vectors. Dideoxy DNA sequencing (19) was carried out using [$^{35}$S]-dATP (Amersham) and buffer gradient gels (20).

Enzyme-linked immunosorbent assay (ELISA)

Sheets of nitrocellulose soaked in 10 mM IPTG were coated with La antigen by induction of confluent phage plaques containing the clonally purified, full-length La cDNA. For more sensitive assays the partially purified β-galactosidase-La fusion protein was used to coat nitrocellulose sheets. Antigen-coated nitrocellulose sheets were treated with a BSA-containing blocking solution (Kirkegaard and Perry Laboratories), and dilutions of human sera were placed in contact with the antigen for 1 hr. The sera were removed and the filters thoroughly washed with buffer containing 0.02M imidazole buffered saline and 0.02% Tween 20 (Kirkegaard and Perry Laboratories). The nitrocellulose sheets were washed for 10 min each in the Tween 20 buffer and twice in phosphate buffered saline (PBS). The antibody-reacted sheets were incubated with lactoperoxidase-conjugated protein A at a concentration of 1 µg/ml for 30 min. After 3 cycles of washing, filters were reacted with 4-chloro-1-naphthol in the peroxidase substrate system (Kirkegaard and Perry) for 10 min.

RESULTS

Isolation and Identification of La-CDNA clones

Initial plaque screening of 500,000 recombinants identified twenty putative La clones. Upon several rounds of purification and rescreening with various La specific autoantibodies, three positive La clones were isolated and confirmed. FIG. 1(a) shows a series of photographs of culture media demonstrating isolation and identification of La cDNA clones by the immunological screening procedure. Recombinant phages were plated initially at a density of approximately 200 pfu/cm2 on 576 cm² plates. A 0.5-cm-diameter agar plug at the position of each of the signals were removed and titered before replating at a density of approximately 20 pfu/cm2 on 9-cm-diameter plates and rescreened. The replating and rescreening process was repeated several times until each phage plug contained clonally purified recombinants, as determined when every plaque on the plate was reactive with La antisera from several different patients.

Figures 1B, 2:
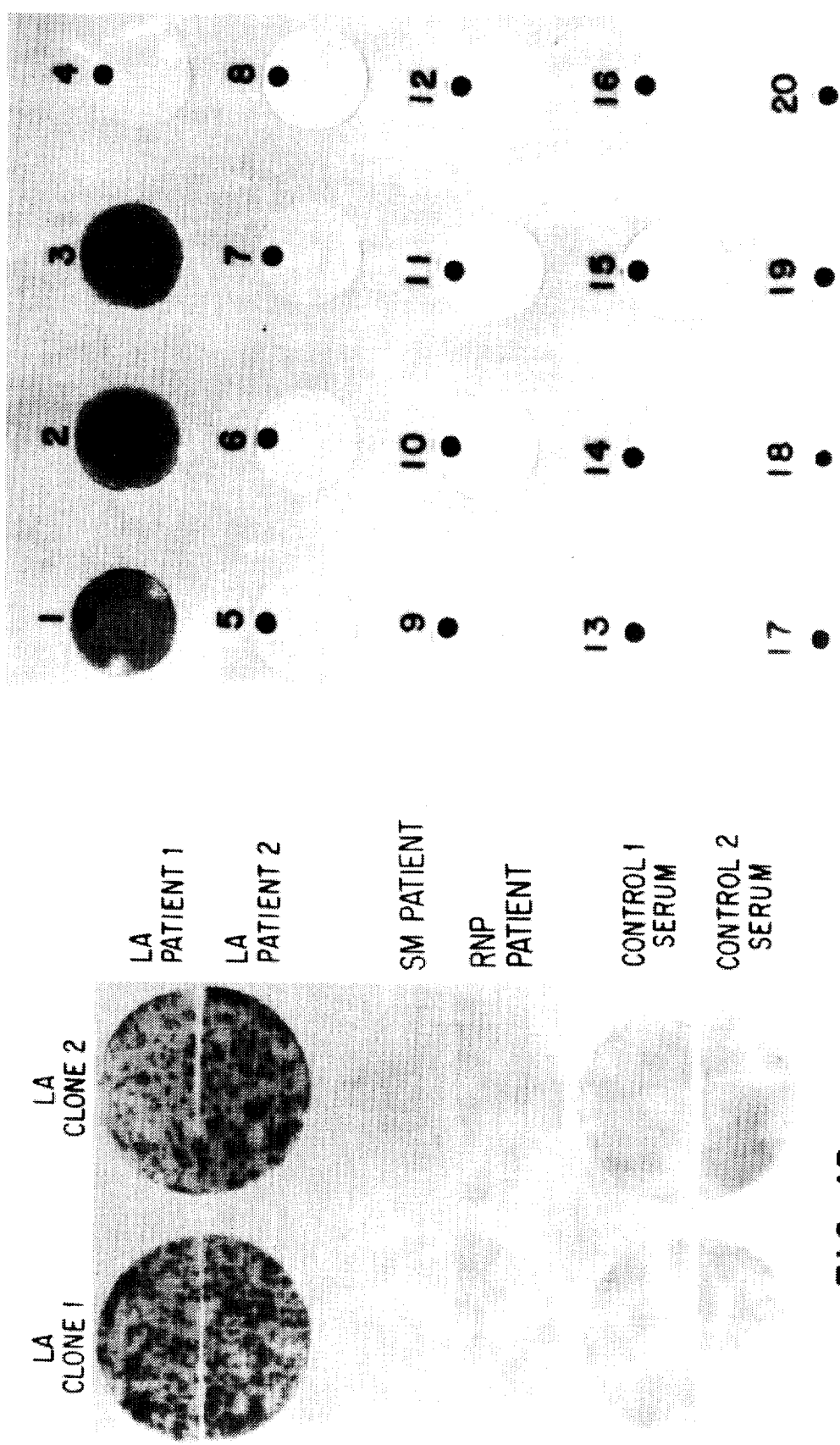
FIG. 1(b) is a series of photographs showing immunological screening of λgtll-LA clones with lupus sera of various specificities.
FIG. 2 is a series of photographs showing enzyme-linked immunosorbent assay (ELISA) using expressed La antigen bound to nitrocellulose and reactive with sera from 18 patients with autoimmune diseases and two normal sera.

When two of the La clones were expressed as λgt11 plaques and analyzed for reactivity with a panel of sera from patients with SLE that did not contain La specific autoantibodies (as assayed by immunoprecipitation of RNA and protein, cell fluorescence (ANA) and counterimmunoelectrophoresis (CIE)) as well as with normal human sera, the data of FIG. 1b were obtained. The sera used exhibited La, Sm and RNP specificities. It is clear that clones that expressed La antigen were only reactive with sera from SLE patients of the La specificity.

These clonally expressed La antigens were further identified by an enzyme-linked immunosorbent assay (ELISA). Results of a typical dot ELISA with one of the La antigen clones are shown in FIG. 2. Sera from 18 SLE patients were analyzed for reactivity with the expressed La antigen. Sera from three SLE-La patients showed a clear positive response while patients with other lupus specificities (Sm, Ro, RNP, Ga, To and unclassified reactivities) and normals showed only a low background of reactivity. Filters were prepared and processed as described in Materials and methods and analyzed by lactoperoxidase linked S. aureus protein A. (1–2) La, (3) La/Ro, (4) Ro, (5) Sm, (6) RNP, (7) SM/RNP, (8) Sm/RNP, (9) unknown SLE, (10) To, (11) RNP, (12) RNP+unknown, (13) Sm/RNP, (14) RNP, (15) unknown SLE, (16) Sm/RNP, (17) unknown SLE (La), (18) unknown SLE (19) normal, (20) normal. In some cases, sera of unknown specificity by ANA and CIE were found by the ELISA to be weakly positive for La protein. Subsequent analysis by RNA and protein precipitations confirmed the presence of La antibodies in these samples (data not shown).

Figure 3:
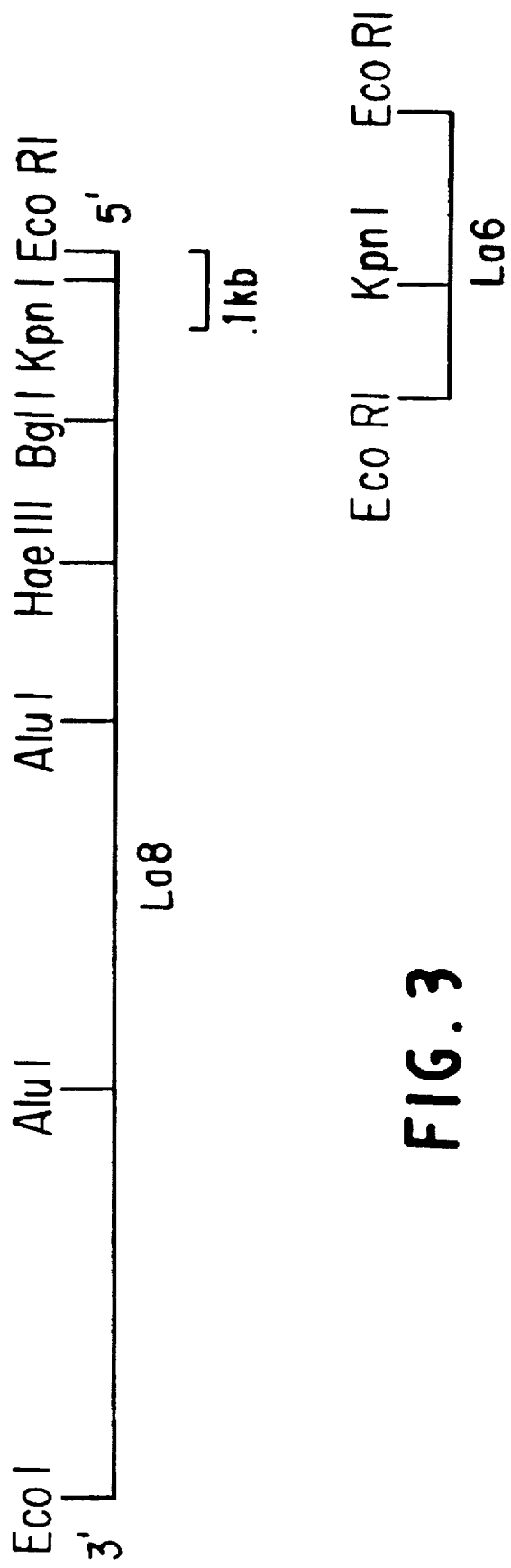
FIG. 3 shows a restriction map of the 1.5 kb La protein cDNA.

Data from DNA—DNA hybridization (not shown) and restriction enzyme analysis indicated that overlapping La clones had been isolated, all of which contained the carboxyl-terminal portion of the coding sequence. The expected length of the coding sequence for the 50,000 dalton human La protein is about 1.5 kb. The largest of the cDNA clones contained an insert of about 1.5 kb and appeared to represent the near full-length coding sequence. A partial restriction map is shown in FIG. 3.

Protein identity by hybrid selection and in vitro translation

Figure 4:
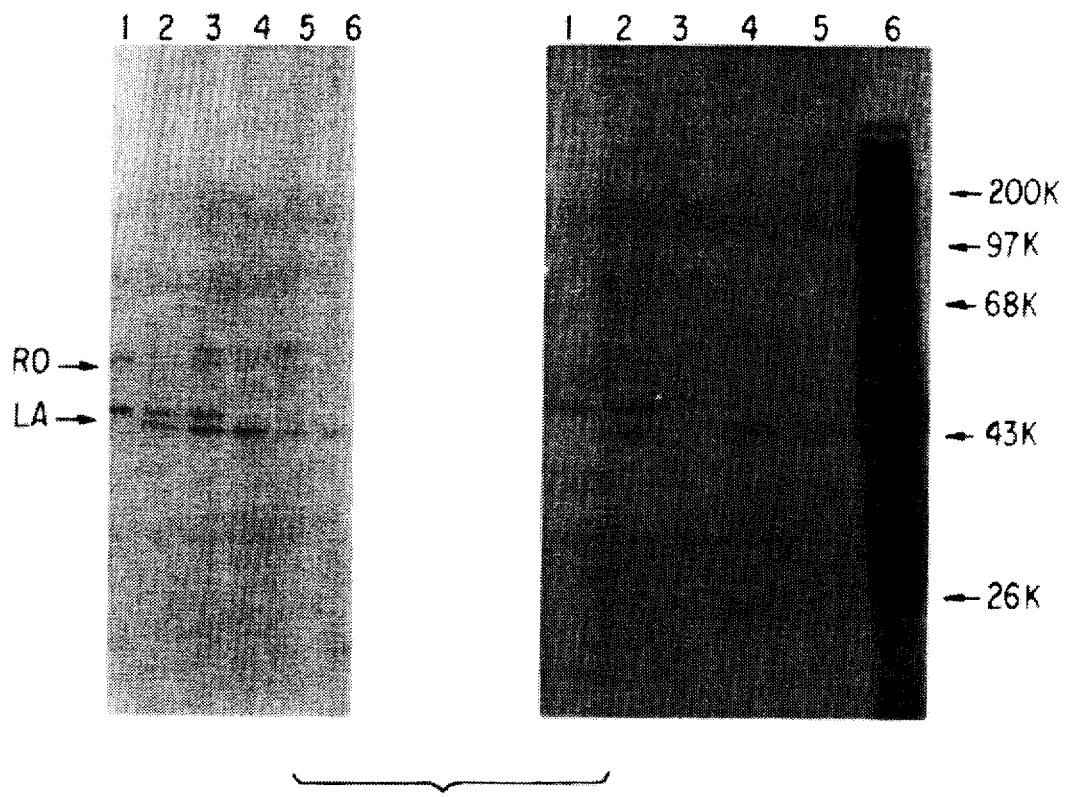
FIG. 4 is a photographic reproduction of a series of acrylamide gel electrophoreses showing in vitro translation of hybrid-selected HeLa-cell mRNA using cDNA for La protein.

To confirm the identity of the cDNA clones, the techniques of hybrid selection and in vitro translation were used. DNA inserts from the λgt11-La clones, subcloned into pBR322, were used for hybrid selection of mRNA from total HeLa cytoplasmic RNA. The selected filter-bound mRNA was eluted and translated in vitro using rabbit reticulocyte lysates. FIG. 4 shows a fluorogragh of the [$^{35}$S]-methionine-labeled products synthesized in vitro, and fractionated on 15% SDS/acrylamide gels.

The various gels are shown in FIG. 4 as follows:

(a) Lane 1, in vivo [$^{35}$S]-labeled HeLa cell proteins immunoprecipitated with lupus sera of the La and Ro specificities. Lane 2, in vitro translated products from Hela mRNA hybrid-selected with La cDNA insert. Lane 3, in vitro translated products from HeLa mRNA hybrid-selected with La cDNA plasmid. Lanes 4 and 5, in vitro translated products from Hela mRNA hybrid-selected with the plasmid pBR322. Lane 6, in vitro translated products using 10 μg of carrier tRNA.

(b) Lane 1, in vivo [35S]-labeled HeLa cell proteins immunoprecipitated with lupus sera of the La specificity. Lane 2, same as lane 3 in (a). Lane 3, translated material from lane 2 immunoprecipitated with anti-La serum. Lane 4, same as lane 4 in (a). Lane 5, same as lane 6 in (a). Lane 6, in vitro translated products using 0.1 μg of total HeLa cell RNA.

Figure 5:
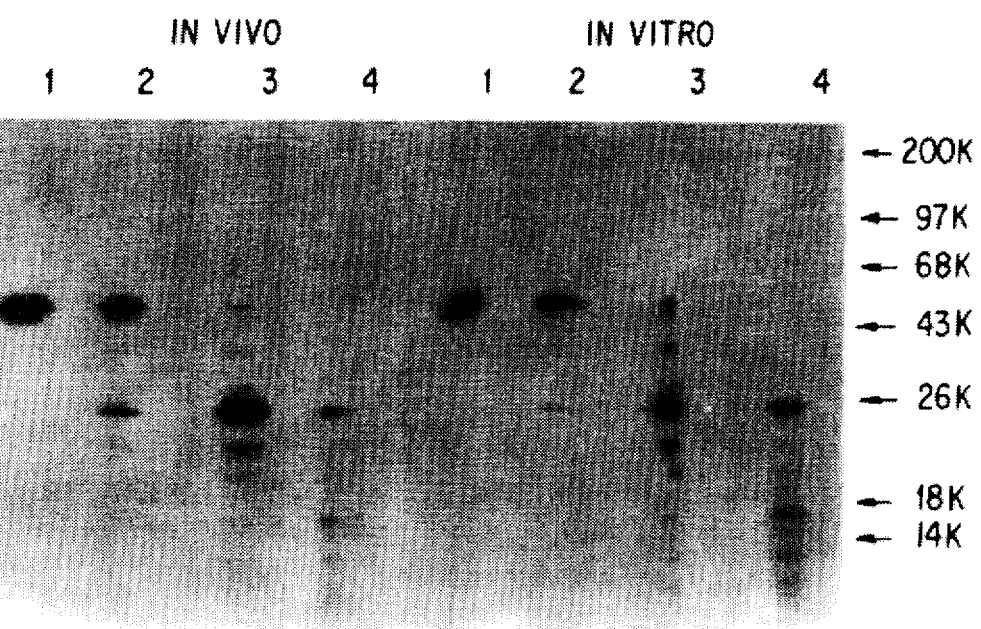
FIG. 5 is a photographic reproduction of partial peptide mapping of the La protein showing in vivo radioactively labeled HeLa-cell La protein.
Figure 6:
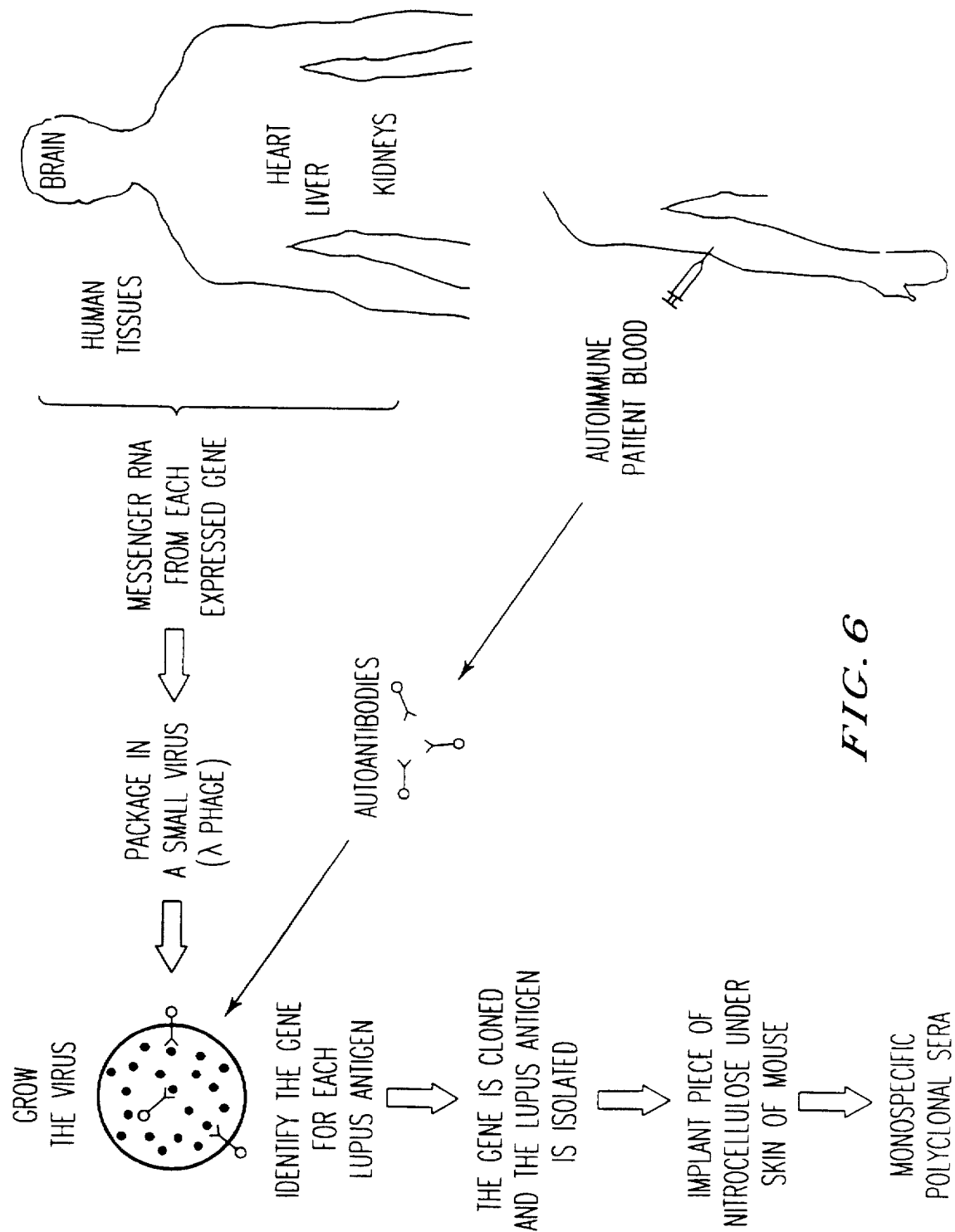
FIG. 6 shows the cloning methodology used in their invention, involving the identification of unique autoimmune patient sera, choice of appropriate human tissue library, screening, purification, authentication of the clone and preparation of animal derived antibodies.

A single protein of approximately 50,000 daltons was the only protein species unique to the La-cDNA selected mRNA (FIG. 4a, lanes 2 and 3: FIG. 4b, lane 2). This protein co-migrated with the in vivo labeled La protein immunoprecipitated by anti-La serum (FIG. 4a and b, lane 1). The in vitro synthesized species was found to be reactive with the same antiserum (FIG. 4b, lane 3). To further demonstrate that the in vitro translated protein was indeed the authentic cellular La protein, hybrid selection and translation and fractionated the products on preparative gels was carried our. Preparative gels were autoradiographed, and the gel slices containing both in vitro and in vivo labeled La protein were transferred to sample wells of a second gel. Using the method of Cleveland et al (17), the samples were subjected to limited proteolysis with S. aureus V8 protease, and the peptides generated were analyzed. FIG. 5 shows a fluorograph of peptide mapping of the La protein synthesized in vitro and in vivo. In vivo r35s]-labeled HeLa cell La protein and the co-migrating protein band synthesized in vitro with rabbit reticulocyte lysates using La cDNA hybrid-selected mRNA were gel purified, digested with varying amounts of S. aureus V8 protease, and analyzed on a 15% SDS/acrylamide gel. Samples were incubated for 30 min. in the stacking gel with lanes 1–4 representing 0, 10, 100 and 1000 ng of protease, respectively. These data demonstrate that the in vitro translated product has the same partial proteolytic profile as the in vivo labeled La protein. Therefore, the cDNA clones code for and express the human La protein.

Mapping of an antigenic site of the La protein

Because λgt11 expresses cDNA inserts in the correct reading frame, as defined by antigenicity, it was possible to determine the amino acid sequence from the DNA sequence starting immediately after the 5' Eco RI cleavage site. The smallest cDNA insert isolated was 390 nucleotides long that included 366 bases coding for the carboxyl terminal 122 amino acids of La protein in addition to 24 nucleotides of noncoding information. The coding sequence of another cDNA insert was found to include only the carboxyl terminal 55 amino acids. Because both cDNA inserts were expressed as β-galactosidase fusion proteins in the λgt11 vector, at least one antigenic site reactive with La antisera resides in this 55-amino-acid region (terminal 12%) of the protein. The nucleotide and amino acid sequences are as follows:

| GGC | TGG | GTA | CCT | TTG | GAG | ATA | ATG | ATA | AAA | 30 |
|---|---|---|---|---|---|---|---|---|---|---|
| gly | trp | val | pro | leu | glu | ile | met | ile | lys | |
| TTC | AAC | AGG | TTG | AAC | CGT | CTA | ACA | ACA | GAC | 60 |
| phe | asn | arg | leu | asn | arg | leu | thr | thr | asp | |
| TTT | AAT | GTA | ATT | GTG | GAA | GCA | TTG | AGC | AAA | 90 |
| phe | asn | val | ile | val | glu | ala | leu | ser | lys | |
| TCC | AAG | GCA | GAA | CTC | ATG | GAA | ATC | AGT | GAA | 120 |
| ser | lys | ala | glu | leu | met | glu | ile | ser | glu | |
| GAT | AAA | ACT | AAA | ATC | AGA | AGG | TCT | CCA | AGC | 150 |
| asp | lys | thr | lys | ile | arg | arg | ser | pro | ser | |
| AAA | CCC | CTA | CTG | AAG | TGA | | | | | |
| lys | pro | leu | leu | lys | TERM | | | | | |

One in-frame termination codon was present beginning at position 166.

This sequence has a high content of hydrophobic amino acids. Hydrophilicity analysis using the method of Hopp and Woods (21) identified a decapeptide from amino acids 40 to 49 with a value of +1.61. The average hydrophilicity of the 55 amino acid antigenic portion was calculated to be +0.3. Based on this method, this decapeptide region has a high probability of being exposed on the surface of the protein and may overlap with an antigenic determinant for La protein. Accordingly, this hexapeptide sequence, glu-asp-lysthr-lys-ile-arg-arg-ser-pro represents for the first time a unique antigenic determinant associated with an autoimmune disease.

The method as described above has also been applied to the production of clones expressing antigens cross-reactive with natural Ro, L-42, Scl, and U2bp antigens.

A deposit has been made with the American Type Culture Collection, 12301 Parklawn Drive, Rockville, Md. 20852, U.S.A. to exemplify this preferred aspect of the invention. The deposit is identified as *E. coli* HB1010-Lab and by its deposit number, ATCC 39984. This strain comprises a pBR322 plasmid having a La antigen gene inserted therein and transformed into *E. coli* HB101.

REFERENCES

1. Tan, E. M. (1982), "Autoantibodies to Nuclear Antigens (ANA): Their Immunobiology and Medicine," in *Advances in Immunology*, Vol. 33, H. Kunkel and F. Dixon, eds., Academic Press, Inc., pp. 167–240.
2. Kurilla, M. G. and Keene, J. D. (1983), *Cell* 34, pp. 837–845.
3. Chambers, J. C., Kurilla, M. G. and Keene, J. D. 1983), *J. Biol. Chem.* 258, pp. 11438–11441.
4. Hendrick, J. P., Wolin, S. L., Rinke, J., Lerner, M. R., and Steitz, J. A. (1981), *Mol. Cell. Biol.* pp. 1138–1149.
5. Rinke, J., and Steitz, J. A. (1982), *Cell* 29, pp. 149–159.
6. Hashimoto, C. and Steitz, J. A. (1983), *J. Biol. Chem.* 258, pp. 1379–1384.
7. Lerner, M. R., Boyle, J. A., Hardin, J. A. and Steitz, J. A. (1981), *Science* 211, pp. 400–402.
8. Francoeur, A. M. and Mathews, M. B. (1982), *Proc. Natl. Acad. Sci. USA* 79, pp. 6772–6776.
9. Rosa, M. D., Gottlieb, E., Lerner, M. R., and Steitz, J. A. (1981), *Mol. Cell. Biol.* 1, pp. 785796.
10. Wilusz, J., Kurilla, M. G., and Keene, J. D. (1983), *Proc. Natl. Acad. Sci. USA* 80, pp. 58275831.
11. Kurilla, M. G., Cabradilla, C. D., Holloway, B. P., and Keene, J. D. (1984), *J. Virol.* 50, 773778.
12. Reddy, R., Henning, D., Tan, E., and Busch, H. (1983), *J. Biol. Chem.* 258, pp. 8352–8356.
13. Mathews, M. B. and Francoeur, A. M. (1984), *Mol. Cell. Biol.* 4, pp. 1134–1140.
14. Stefano, J. E. (1984), *Cell* 36, pp. 145–154.
15. Young, R. A. and Davis, R. W. (1983), *Science* 222, pp. 778–782.
16. Laemmli, U. K. (1970), *Nature* (London) 227, pp. 680–685.
17. Maniatis, T., Fritsch, E. F., and Sambrook, J. (1982), *Molecular Cloning: A Laboratory Manual* (Cold Spring Harbor Laboratory, Cold Spring Harbor, N.Y.).
18. Cleveland, D. W., Fischer, S. G., Kirschner, M. W., and Laemmli, U. K. (1977), *J. Biol. Chem.* 252, pp. 1102–1106.
19. Sanger, F., Coulson, A. R., Barrell, B. G., Smith, A. J. H., and Roe, B. A. (1980), *J. Mol. Biol.* 143, 161–178.
20. Biggin, M.D., Gibson, T. J. and Hong, G. F. (1983), *Proc. Natl. Acad. Sci.* 80, pp. 3963–3965.
21. Hopp, T. P. and Woods, K. R. (1981), *Proc. Natl. Acad. Sci. USA* 78 pp. 3824–3828.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A biologically pair peptide comprising the sequence:

| Tyr | Lys | Ile | Pro | Val | Ile | Glu | Asn | Leu | Gly | Ala | Thr | Leu |
|---|---|---|---|---|---|---|---|---|---|---|---|---|
| Asp | Gln | Phe | Asp | Ala | Ile | Asp | Phe | Ser | Asp | Asn | Glu | Ile |
| Arg | Lys | Leu | Asp | Gly | Phe | Pro | Leu | Leu | Arg | Arg | Leu | Lys |
| Thr | Leu | Leu | Val | Asn | Asn | Asn | Arg | Ile | Cys | Arg | Ile | Gly |
| Glu | Gly | Leu | Asp | Gln | Ala | Leu | Pro | Cys | Leu | Thr | Glu | Leu |
| Ile | Leu | Thr | Asn | Asn | Ser | Leu | Val | Glu | Leu | Gly | Asp | Leu |
| Asp | Pro | Leu | Ala | Ser | Leu | Lys | Ser | Leu | Thr | Tyr | Leu | Ser |
| Ile | Leu | Arg | Asn | Pro | Val | Thr | Asn | Lys | Lys | His | Tyr | Arg |
| Leu | Tyr | Val | Ile | Tyr | Lys | Val | Pro | Gln | Val | Arg | Val | Leu |
| Asp | Phe | Gln | Lys | Val | Lys | Leu | Lys | Glu | Arg | Gln | Glu | Ala |
| Glu | Lys | Met | Phe | Lys | Gly | Lys | Arg | Gly | Ala | Gln | Leu | Ala |
| Lys | Asp | Ile | Ala | Arg | Arg | Ser | Lys | Thr | Phe | Asn | Pro | Gly |
| Ala | Gly | Leu | Pro | Thr | Asp | Lys | Lys | Lys | Gly | Gly | Pro | Ser |
| Pro | Gly | Asp | Val | Glu | Ala | Ile | Lys | Asn | Ala | Ile | Ala | Asn |
| Ala | Ser | Thr | Leu | Ala | Glu | Val | Glu | Arg | Leu | Lys | Gly | Leu |
| Leu | Gln | Ser | Gly | Gln | Ile | Pro | Gly | Arg | Glu | Arg | Arg | Ser |
| Gly | Pro | Thr | Asp | Asp | Gly | Glu | Glu | Met | Glu | Glu | Asp |
| Thr | Val | Thr | Asn | Gly | Ser. | | | | | | |